(12) United States Patent
Tanaka et al.

(10) Patent No.: US 8,552,399 B2
(45) Date of Patent: Oct. 8, 2013

(54) APPARATUS FOR PRODUCING PHOTOCATALYTIC REACTION WATER

(75) Inventors: Kenichiro Tanaka, Kitakyushu (JP);
Licca Tanaka, Kitakyushu (JP); Mizuki Kawakatsu, Fukutsu (JP)

(73) Assignee: K2R Co., Ltd., Fukuoka (JP)

( * ) Notice: Subject to any disclaimer, the term of this patent is extended or adjusted under 35 U.S.C. 154(b) by 182 days.

(21) Appl. No.: 12/083,435

(22) PCT Filed: Oct. 11, 2006

(86) PCT No.: PCT/JP2006/320346
§ 371 (c)(1),
(2), (4) Date: Jun. 12, 2008

(87) PCT Pub. No.: WO2007/043592
PCT Pub. Date: Apr. 19, 2007

(65) Prior Publication Data
US 2009/0230038 A1 Sep. 17, 2009

(30) Foreign Application Priority Data

Oct. 11, 2005 (JP) .................. 2005-297021
Nov. 9, 2005 (JP) .................. 2005-325271

(51) Int. Cl.
*G01N 21/01* (2006.01)
*C02F 1/32* (2006.01)

(52) U.S. Cl.
USPC ...... 250/436; 250/438; 210/748.11; 210/758; 210/763; 210/764; 210/192; 210/205

(58) Field of Classification Search
USPC ............... 210/748.14, 748.03, 748.04, 748.1, 210/748.11, 748.12, 748.13, 748.15, 192, 210/219, 503, 504, 505, 758, 763, 764, 210/205; 250/430, 432 R, 435, 436, 438
See application file for complete search history.

(56) References Cited

U.S. PATENT DOCUMENTS

| | | | |
|---|---|---|---|
| 5,032,241 A * | 7/1991 | Robertson et al. ........ | 210/748.14 |
| 5,130,031 A * | 7/1992 | Johnston .................. | 210/748.13 |
| 5,302,356 A * | 4/1994 | Shadman et al. ............ | 210/192 |
| 5,395,522 A * | 3/1995 | Melanson et al. ............ | 210/259 |
| 2002/0033368 A1 | 3/2002 | Nasu et al. | |
| 2003/0209501 A1 | 11/2003 | Leung | |

FOREIGN PATENT DOCUMENTS

| | | |
|---|---|---|
| EP | 1 178 014 A1 | 2/2002 |
| EP | 1 686 095 A1 | 8/2006 |
| JP | A-03-200705 | 9/1991 |
| JP | A-05-309267 | 11/1993 |
| JP | A-2000-024494 | 1/2000 |
| JP | A-2000-061458 | 2/2000 |
| JP | A-2000-210659 | 8/2000 |
| JP | A-2000-262855 | 9/2000 |

(Continued)

*Primary Examiner* — Lucas Stelling
(74) *Attorney, Agent, or Firm* — Oliff & Berridge, PLC

(57) ABSTRACT

The present invention provides an apparatus for producing photocatalytic reaction water through a photocatalytic reaction, which can produce water containing a satisfactory amount of active oxygen species, can eliminate microorganisms, parasites or protozoa, shows high oxidizing ability for a prolonged period of time, can reduce the power requirements, is small in size, and is applicable to various devices. A photocatalyst is radiated with light emitted from a light source to produce active oxygen species, and the active oxygen species is diffused in water, whereby the water is provided with functions of the active oxygen species. An oxidation reaction with the water is utilized to perform at least one selected from the elimination of microorganisms, the elimination of parasites, and the elimination of protozoa.

7 Claims, 18 Drawing Sheets

(56) References Cited

FOREIGN PATENT DOCUMENTS

| | | |
|---|---|---|
| JP | A-2000-312830 | 11/2000 |
| JP | A-2001-161212 | 6/2001 |
| JP | A-2001-232380 | 8/2001 |
| JP | A-2001-259663 | 9/2001 |
| JP | A-2001-327961 | 11/2001 |
| JP | A-2002-045871 | 2/2002 |
| JP | A-2003-26406 | 1/2003 |
| JP | A-2003-154379 | 5/2003 |
| JP | A-2003-285085 | 10/2003 |
| JP | A-2005-021794 | 1/2005 |
| WO | WO 96/36565 A1 | 11/1996 |
| WO | WO 03/027021 A2 | 4/2003 |
| WO | WO 2004/108605 A1 | 12/2004 |

\* cited by examiner

APPARATUS FOR PRODUCING PHOTOCATALYTIC REACTION WATER

TECHNICAL FIELD

The present invention relates to an apparatus for producing photocatalytic reaction water which can efficiently generate a large quantity of active oxygen species in water by making use of the photocatalytic reaction thereby eliminating microorganisms, parasites or protozoa by bringing them into contact with water containing active oxygen species.

BACKGROUND ART

Conventionally, water having sterilization ability or ability to oxidize a material is used in places where the hygienic environment is emphasized such as a medical establishment, a food plant, a public bath house, a pool or the like.

Examples of such water which are usually popularly used are ozone water in which ozone ($O_3$) is dissolved and water processed by an ultra violet sterilization lamp.

However, it has been pointed out that a large quantity of ozone leaks into the atmosphere from an ozone generator which generates ozone water thus giving rise to possibility of adversely affecting the environment or the like. Further, there also arise drawbacks such as the spreading of the odor peculiar to ozone or a large quantity of power consumption at the time of generation of ozone and hence, there exists tendency that the use of ozone has been recently limited.

On the other hand, it has been also known that active oxygen species which are generated by exciting a photocatalytic reaction by radiating light to a photocatalytic body possess a function of sterilizing microorganisms or a function of decomposing various organic chemical substances by oxidation in the extreme vicinity of a surface of the photocatalytic body (usually, 40 nm). That is, although being observed only in the extreme vicinity of the photocatalytic body, these active oxygen species having high reactivity such as a super oxide anion radical ($O_2^-$) or hydro-oxi radical (OH.) are dissolved in water due to contact with water, and transform cell membranes, functional protein, genes or the like of microorganisms or viruses, thus are capable of stopping the survival function or propagation function of microorganisms or viruses.

Accordingly, for example, as shown in FIG. 17 and FIG. 18, there has been proposed a water treatment device having the following constitution for sterilizing the microorganisms in water. That is, an agitating shaft 54 is arranged at a center portion of a cylindrical tank 53 having a water inlet port 51 and a water outlet port 52. Agitating blades 56 each having a mesh-like photocatalytic body 55 are arranged outwardly in the radial direction around the agitating shaft 54. A blacklight 57 for ultra violet radiation is arranged on an inner wall of the tank at a predetermined position. By rotating the agitating shaft 54, a quantity of ultra violet rays which impinge on the photocatalytic body 55 can be increased (see, patent document 1, for example).

According to this water treatment device, the radiation efficiency of ultra violet rays to the photocatalytic body 55 can be enhanced and agitating blades 56 can agitate water and hence, it is possible to sterilize the microorganisms by bringing the microorganisms into contact with active oxygen species generated on a surface of the photocatalyst whereby organic substances in water may be decomposed.

Further, as one of fields which have conventionally required the sterilization of microorganisms, the cultivation of fish is often mentioned.

In general, edible fish are cultivated by extending a fish net in sea water to form a fish preserve, and fish such as seriola, three line grunt or tiger puffer are fed and grown inside the fish reserve.

Such fish cultivation can efficiently acquire by plan various targeted fish compared to the harvesting of fish naturally swimming in the ocean thus contributing to the stable supply of fish to consumers.

Further, the kinds of fish which can be cultivated have increased recently and, at the same time, fish having quality compatible to the quality of natural fish can be cultivated and hence, the steady development of the cultivation industry is expected from now on.

However, in carrying out the fish cultivation, fish are fed and grown in a relatively small fish preserve and hence, once sick fish suffering from microorganisms or parasites appear in the fish preserve, other fish in the fish preserve are infected by the sick fish thus giving rise to possibility that the number of sick fish or dead fish will increase one after another.

Particularly, in fish cultivation which advertises the efficiency and ease of planning as advantages thereof, the massive spread of sick fish or dead fish due to parasites causes immense damage to the cultivation business leading to confusion in supply of fish to markets.

Fish parasites which bring about such fish sickness can be, in general, classified into two kinds of parasites, that is, ectoparasites represented by *Benedemia seriola*, *Heteraxine heterocerca*, and endoparasites represented by lumen endoparasites such as anisakis, organization endoparasites blood vessel trematode such as myxosporidia.

These parasites are further sub-classified depending on the kind of fish and various studies have been made with respect to respective host specificities.

In general, the influence of parasites on the host is mainly attributed to respiration disorder and maintenance management disorder of body fluid attributed to osmotic pressure failure.

With respect to endoparasites such as blood vessel trematode, rather than a drawback caused by the parasite per se, it is necessary to focus on a drawback that the parasite lays eggs and these eggs clog a fine blood vessel of a gill of fish when a large quantity of eggs is discharged into the fine blood vessel thus suffocating fish.

Further, the ectoparasites adhering to fish suck blood from the host at adhering positions and acquire nutrition from the host. The ectoparasites which adhere to epithelium cause an epithelial cell damage thus damaging the fish body parasitized with ectoparasites. Particularly, when the gill is infected with the ectoparasites, this infection causes peeling-off of a respiratory epithelial cell, the inflammation attributed to hyperplasia and a rod-shaped change and these changes are irreversible thus causing the vegetative growth failure attributed to respirational disorder.

Particularly, ectoparasites often adhere to a portion of the fish body where sea water is in contact and hence, there exists high possibility that ectoparasites float per se and eggs thereof in sea water and infect other fish. In this manner, ectoparasites are considered to be one of parasites which cause large damages on the cultivation business.

Accordingly, as a means for preventing or curing sickness attributed to infection of ectoparasites, there has been known a following method (see patent document 2, for example). That is, when ectoparasites are *Benedemia seriola*, a fresh water bath is particularly effective to protect marine fish. When ectoparasites are *Heteraxine heterocerca*, porous carriers impregnated with hydrogen peroxide water are scattered in a fish preserve to protect marine fish. Due to the performance of hydrogen peroxide, parasites or microorganisms are emasculated thus preventing and curing sickness attributed to infection of ectoparasites.

According to this method which uses hydrogen peroxide water, it is possible to attenuate possibility that cultivated fish die out due to parasites or microorganisms.

However, the above-mentioned water treatment device which includes the agitating blades requires large agitating blades for enhancing the efficiency of photocatalytic reaction. Accordingly, to produce water containing a sufficient quantity of active oxygen, there exists a drawback that the device per se becomes large-sized. Further, the oxidizing ability continues for an extremely short time, that is, $10^{-6}$ second and hence, a reaction phase takes only in an extremely limited and extremely narrow region of the photocatalytic body leading to the acquisition of insufficient sterilization effect.

Further, although the device may be miniaturized by miniaturizing the photocatalytic body, lowering of photocatalytic reaction efficiency is not overcome and hence, the reduction of the device is not realized at present.

Still further, in the large-sized device, to drive the agitating shaft, large electric power sufficient to cope with water resistance is necessary and hence, the device is not desirable also from a viewpoint of energy efficiency.

Further, as a photocatalytic body provided to the agitating blades, a photocatalytic body which applies titania coating to a surface of fiber-like aluminum is exemplified. However, the mere application of titania coating to the surface of fiber-like aluminum exhibits poor photocatalytic reaction and hence, it is difficult to efficiently produce water containing activated oxygen.

Further, in the above-mentioned method which treats the cultivated fish with hydrogen peroxide water (referred to as hydrogen peroxide water bath in general), a strong oxidization power of hydrogen peroxide affects the cultivated fish per se. That is, it is not deniable that this method is directed, rather than to the recovery of fish by reducing parasites adhering to the cultivated fish, to the elimination of sickness-weakened fish with parasites and the revival of only strong fish.

The weakened fish dead due to scattering of hydrogen peroxide reduces a catch quantity of cultivated fish leading to the lowering of cultivation efficiency. It is apparent that if parasites can be eliminated from the fish infected with parasites while assuring the safety of such fish, the catch quantity of cultivated fish can be increased leading to the lowering of distribution prices of fish as well as the assurance of safety of foods.

Further, the effective concentration of hydrogen peroxide to be scattered in sea water is required to exhibit the high concentration up to 200 to 3000 ppm. Although hydrogen peroxide is diluted, in the same manner as a conventional balnea medicata method such as a formalin bath, hydrogen peroxide is directly flown out, scattered and thrown away in the ocean. Hydrogen peroxide also affects other marine organisms besides the cultivated fish. Accordingly, the cultivation of fish using hydrogen peroxide is hardly preferable from a viewpoint of environment, and the influence of hydrogen peroxide on human being is not yet determined.

Still further, to achieve a parasite elimination effect, a large quantity of hydrogen peroxide agent becomes necessary, and a cost necessary for preparation of hydrogen peroxide and man-power necessary for transportation of hydrogen peroxide impose a large burden on staffs in charge of such labors.

In the cultivation business which has such drawbacks, there has been a demand for an apparatus and method for producing photocatalytic reaction water for eliminating parasites which do not use medicines which remain in sea water, which do not damage cultivated fish, and do not influence the environment.

Accordingly, inventors of the present invention have made extensive studies on an apparatus for producing photocatalytic reaction water which can produce water containing sufficient quantity of active oxygen species, can eliminate microorganisms and parasites, can maintain strong oxidation ability, can save power, can be formed small, and is applicable to various devices, and have made the present invention.

[Patent document 1] JP-A-2001-327961
[Patent document 2] JP-A-03-200705

DISCLOSURE OF INVENTION

To overcome the above-mentioned drawbacks, an apparatus for producing photocatalytic reaction water according to the present invention is configured such that light from a light source is radiated to a photocatalytic body to generate active oxygen species, and the active oxygen species are diffused in water thus imparting functions of active oxygen species to water whereby an oxidation reaction with the water is utilized to perform at least one from the elimination of microorganisms, the elimination of parasites, and the elimination of protozoa or the like.

The present invention is also characterized by following technical features.

(1) The apparatus for producing photocatalytic reaction water according to the present invention is also characterized in that the photocatalytic body is arranged around the light source for exciting the photocatalytic body.

(2) The apparatus for producing photocatalytic reaction water according to the present invention is also characterized in that the apparatus includes a photocatalytic reaction reservoir, a water supply pump which supplies water into the photocatalytic reaction reservoir, and a water discharge circuit which discharges photocatalytic reaction water from the photocatalytic reaction reservoir, wherein the photocatalytic reaction reservoir arranges, in the inside of a water reservable sealed container, the photocatalytic body which generates active oxygen in water reserved in the sealed container, the light source which radiates light for exciting the photocatalytic body, and a diffusion means which diffuses the active oxygen species generated on a surface of the photocatalytic body in water, and an inner wall surface of the sealed container is formed of a mirror surface which reflects the light.

(3) The apparatus for producing photocatalytic reaction water according to the present invention is also characterized in that the light source for exciting the photocatalytic body utilizes sun light and/or artificial light.

(4) The apparatus for producing photocatalytic reaction water according to the present invention is also characterized in that in using the sun light as the light source for exciting the photocatalytic body, a reflector such as optical fibers or a prism is used for directly radiating light to the photocatalytic body in water.

(5) The apparatus for producing photocatalytic reaction water according to the present invention is also characterized in that as the light source for exciting the photocatalytic body, an ultra violet ray radiation lamp in using artificial light radiates ultra violet rays having a wavelength ranging from at least 350 to 370 nm.

(6) The apparatus for producing photocatalytic reaction water according to the present invention is also characterized in that the photocatalytic body is an organic or inorganic filter body and a surface of the filter body is covered with a titania thin film.

(7) The apparatus for producing photocatalytic reaction water according to the present invention is also characterized in that the photocatalytic body is an aluminum-based metal filter body and a surface of the filter body is covered with a titania thin film.

(8) The apparatus for producing photocatalytic reaction water according to the present invention is also characterized in that the photocatalytic body is formed of a metal-made fiber body having a surface thereof preliminarily covered with an alumina film, and a surface of the photocatalytic body is covered with a titania thin film.

(9) The apparatus for producing photocatalytic reaction water according to the present invention is also characterized in that the alumina film of the metal-made fiber body is formed by heating the alumina film up to a temperature one half of a melting point of the aluminum-based metal which constitutes the metal fiber body at a rate of 5° C./min and, thereafter, by heating the metal-made fiber body up to a temperature immediately below the melting point of the aluminum-based metal.

(10) The apparatus for producing photocatalytic reaction water according to the present invention is also characterized in that the photocatalytic body is formed of a glass-made fiber body, a ceramics-made fiber body or a non-woven fabric having a surface thereof covered with a titania thin film.

(11) The apparatus for producing photocatalytic reaction water according to the present invention is also characterized in that titanium oxide which constitutes the titania thin film contains the anatase-type or rutile-type crystal structure.

(12) The apparatus for producing photocatalytic reaction water according to the present invention is also characterized in that a diffusion means which diffuses the active oxygen species in water is ultrasonic waves of 100 kHz or more generated by an ultrasonic wave oscillator and/or a water flow generated by a water fan for moving the photocatalytic body and/or water.

(13) The apparatus for producing photocatalytic reaction water according to the present invention is also characterized in that water which is brought into contact with the photocatalytic body is water containing oxygen at high concentration.

(14) The apparatus for producing photocatalytic reaction water according to the present invention is also characterized in that water containing oxygen at high concentration is produced by bringing water into contact with at least one of oxygen, air and ozone.

(15) The apparatus for producing photocatalytic reaction water according to the present invention is also characterized in that a sterilizing action is generated by a sterilizing lamp which radiates ultra violet rays having a wavelength ranging from 254 to 265 nm upstream of a position where a sterilizing action by the photocatalyst is generated, downstream of the position or at the position.

BEST MODE FOR CARRYING OUT THE INVENTION

Figure 1:
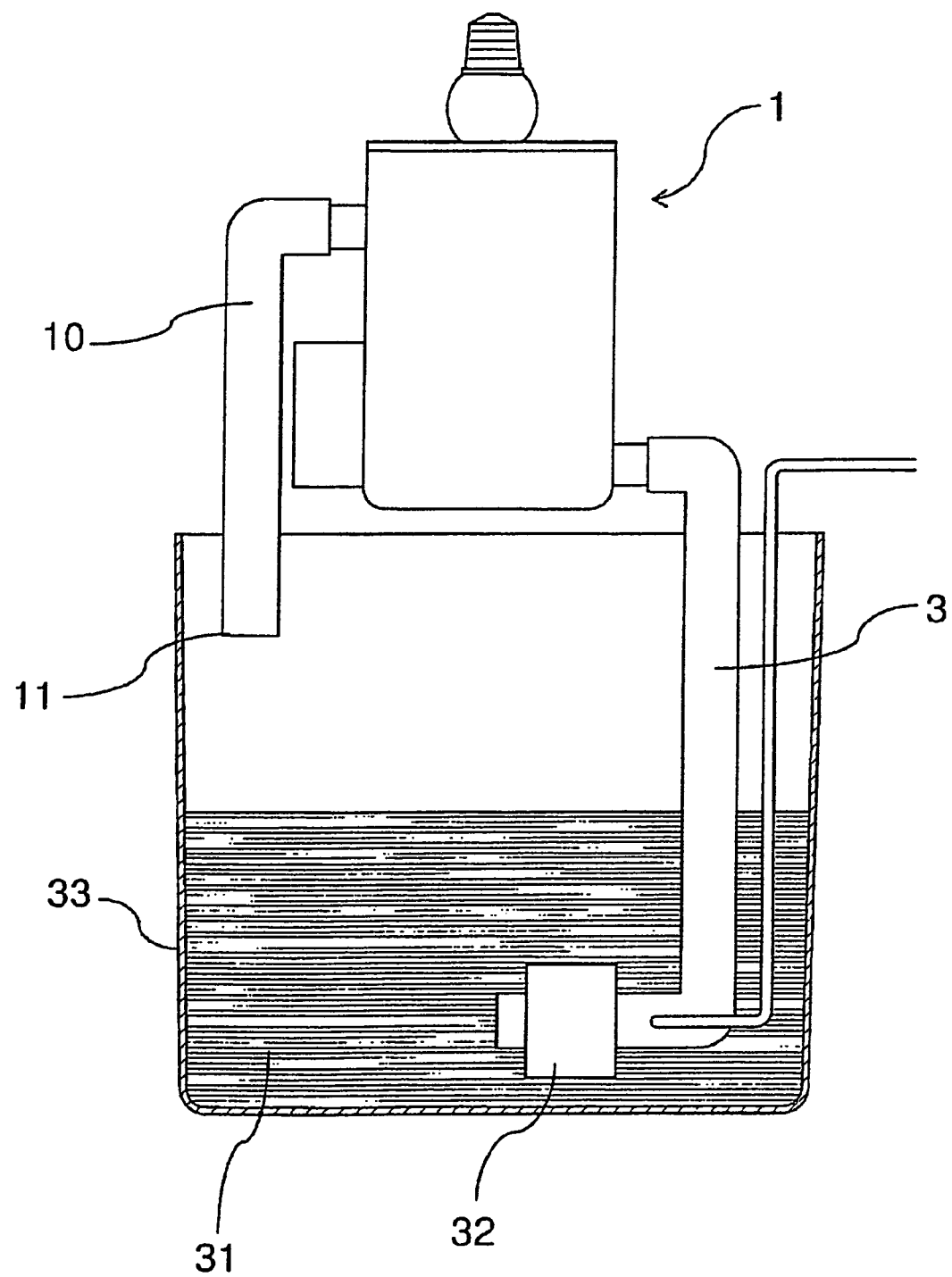
FIG. 1 is an appearance view of an apparatus for producing photocatalytic reaction water according to the present invention.

An apparatus for producing photocatalytic reaction water according to the present invention is configured such that light from a light source is radiated to a photocatalytic body to generate active oxygen species, and the active oxygen species are diffused in water thus imparting functions of active oxygen species to water whereby an oxidation reaction with the water is utilized to perform at least one from the elimination of microorganisms, the elimination of parasites adhering to marine organisms, and the elimination of protozoa or the like.

That is, in the apparatus for producing photocatalytic reaction water according to the present invention, by diffusing the active oxygen species generated on a surface of the photocatalytic body in water, the elimination or sterilization of microorganisms and the elimination of protozoa or the like is performed using water as a medium.

Further, together with such an advantageous effect, by diffusing the active oxygen species generated on a surface of the photocatalytic body in water, the elimination of parasites adhering to fish body is performed using water as a medium.

By forming a titania thin film having a photocatalytic ability on a surface of the photocatalytic body, due to the impingement of ultra violet rays radiated from an ultra violet ray lamp on the titania thin film, the titania thin film is excited thus activating the photocatalytic body.

On the surface of the activated photocatalytic body, the energy (hv) of the ultra violet rays radiated from the ultra violet ray lamp excites titanium oxide (TiO$_2$) which constitutes the titania thin film so that water filled in the apparatus for producing photocatalytic reaction water is brought into contact with the photocatalytic body thus generating active oxygen species. A reaction which generates the active oxygen species by bringing water into contact with the excited photocatalytic body is referred to as a primary reaction.

The primary reaction is considered to occur as follows.

$$TiO_2 + hv \rightarrow e^- + h + VB$$

$$h + VB \rightarrow h + tr$$

$$O_2 + e^- \rightarrow O_2 .-$$

$$O_2.- + h + VB(h + tr) \rightarrow O_2$$

$$OH^- + h + VB \rightarrow HO.$$

Next, the active oxygen species which are generated by the primary reaction exhibit the high reaction ability and hence, the active oxygen species react with each other, and the active oxygen species react with substances or ions dissolved in water thus generating a further product. Here, the reaction which allows the active oxygen species generated by the primary reaction with the substances or ions dissolved in water is referred to as a secondary reaction.

The secondary reaction is considered to occur as follows, for example.

$$O^{2-} + O^{2-} + 2H^+ \rightarrow H_2O_2 + O_2 \text{ (production of hydrogen peroxide water)}$$

It is considered that, except for ultrapure water which contains no other ions, water which is present in an ordinary environment assumes a state in which the water contains a trace amount of atomic ions. Particularly, since chlorine sterilization is applied to water such as tap water, it is considered that a following secondary reaction occurs.

$$HCl + O_2.- + OH^- \rightarrow ClO_2 + H_2O \text{ (production of chlorous acid)}$$

$$ClO_2 + 2OH^- \rightarrow HOCl + H_2O \text{ (production of hypochlorous acid)}$$

Further, in an environment such as river, sea water or the like in which organisms are present, water contains ammonia and hence, it is considered that a following secondary reaction occurs in the same manner.

$$NH_3 + OH^- \rightarrow NO^- + 2H_2O \text{ (production of oxygen nitride ions)}$$

It is needless to say that more secondary reactions occur in addition to the above-mentioned reactions. The secondary reaction products produced in these manners are also, in the same manner as the primary reaction products (active oxygen species), substances which possess a bacteria elimination effect and a parasites or protozoa elimination effect attributed to the photocatalytic reaction water.

Particularly, when water which is in contact with the photocatalytic body is sea water or an aqueous solution in which predetermined substances are dissolved, a large number of kinds of secondary reaction products can be produced.

However, since the conventional method cannot sufficiently diffuse the active oxygen species generated by the photocatalytic body, unless the active oxygen species generated on a surface of the photocatalyst are allowed to directly act on microorganisms or the like adhering to a surface of the photocatalytic body without the presence of a medium there between so as to eliminate only the microorganisms or parasites which are deposited on the surface of the exited photocatalytic body, the method cannot enjoy the bacteria elimination effect and the protozoa and parasites elimination effect. The present invention is characterized by the constitution which allows the acquisition of the bacteria elimination effect, the bacteria sterilization effect, and the elimination of protozoa and parasites due to the active oxygen species even at a place remote from the photocatalytic body. Hereinafter, water which functions as the medium and contains active oxygen species as described above is referred to as "photocatalytic reaction water".

Here, the light is not limited to visible light, and is a conceptual term which also includes ultra violet rays having a short wavelength.

Further, as a light source for exciting the photocatalytic body, sun light and/or artificial light can be used. For example, when sun light is used as such a light source, it is possible to reduce a cost for exciting the photocatalytic body. Further, it is also possible to radiate ultra violet-ray energy which is stronger than energy obtained by artificial light to the photocatalytic body. In radiating light to the photocatalytic body arranged in water, by making use of a reflector such as optical fibers or a prism, the sun light or the artificial light may be introduced into water for directly radiating light to the photocatalytic body in water.

The photocatalytic body may be made of titanium oxide (titania) having a rutile-type or anatase-type crystal phase.

With respect to the photocatalytic body made of titanium oxide, titania may be applied to a fiber-like carrier by dip coating thus forming a highly efficient photocatalytic body having an enlarged surface area.

Here, metal containing aluminum on the order of No. 1000 to No. 7000 or the like, for example (herein after, also referred to as aluminum-based metal) may be favorably used as the fiber-like carrier. However, with the use of the alumina metal fiber body formed by heating aluminum-based metal, titania is densely applied to the carrier by coating and hence, it is possible to further enhance the durability of the photocatalytic body.

The alumina metal fiber body may be formed by heating metal containing aluminum which constitutes a carrier up to a predetermined temperature at a temperature elevation rate of 5° C./min and, thereafter, by heating the metal up to a temperature immediately below a melting point of the metal fiber body.

Here, the predetermined temperature can be calculated using the following formula.

predetermined temperature (° C.)=melting point temperature (° C.) of metal containing aluminum/2

To explain the photocatalytic body in more detail, by applying dip coating to a metal fiber body whose surface is covered with alumina and forms a carrier, it is possible to form a thin dense-structure titania film on an alumina film thus realizing the formation of uniform titania thin film. With the excitation of the uniform titania thin film using ultra violet rays, the photocatalytic reaction can be performed more efficiently and hence, it is possible to generate more active oxygen species.

Here, the alumina film of the metal fiber body is formed by the following manner. That is, the aluminum-based metal fiber is gently heated at a temperature elevation rate equal to or less than 5° C./minute until the temperature reaches approximately half of the melting point temperature to oxidize a surface of the aluminum-based metal fiber. Thereafter, the aluminum-based metal fiber is heated up to a temperature immediately below the melting point for oxidizing a deeper layer thus forming an artificial oxide film which sufficiently exhibits a function of alumina fiber. Here, aluminum-based metal implies both of aluminum and aluminum alloy.

That is, while protecting the metal fiber body using the oxide film formed by heating the metal fiber body up to the temperature approximately half of the melting point of the aluminum-based metal, the metal fiber body is heated up to the temperature immediately below the melting point thus forming the homogeneous alumina film. Further, by heating the metal fiber body up to the melting point of the aluminum-based metal constituting the metal fiber body or more, it is possible to form an extremely stabilized oxide film. Accordingly, when the titania thin film is formed on the metal fiber body, it is possible to enhance the adhesiveness between the titania thin film and the metal fiber body.

Further, the metal fiber body which is formed such that the oxide film is formed by heating the metal fiber body up to the temperature approximately half of the melting point of the aluminum-based metal, the metal fiber body is heated up to the temperature immediately below the melting point while protecting the metal fiber body by the oxide film and, thereafter, the metal fiber body is baked at a temperature which exceeds the melting point of the aluminum-based metal. The metal fiber body formed in this manner can maintain a fiber state even when the metal fiber body is elevated up to the temperature in the vicinity of the melting point of alumina thus exhibiting functions as alumina fiber as the ability of the fiber. To form a rutile-type fiber which causes a rutile-type photocatalytic reaction in the photocatalytic body, it is necessary to bake the metal fiber body at a temperature of 750° C. which exceeds the melting point of the aluminum-based metal or more in the dip coating step. However, the extremely stable alumina metal fiber body which forms the homogeneous alumina film thereon can form the rutile-type titania fiber having high adhesiveness with the titania thin film while maintaining a fiber state.

In this manner, by increasing the adhesiveness between the titania thin film and the metal fiber body, it is possible to form the photocatalytic body having sufficient durability while preventing the titania thin film from being peeled off from the metal fiber body even in an ultrasonic-wave environment.

By forming the alumina metal fiber body by heating the fiber body made of metal containing aluminum in this manner, the alumina metal fiber body having the dense alumina film can be formed and hence, the durability and the catalytic efficiency of the photocatalytic body can be further enhanced.

Here, for example, a means for diffusing the active oxygen species in water may use ultrasonic waves.

The effects of the ultrasonic wave oscillator are as follows. That is, air and oxygen supplied to the apparatus are mixed into circulating water and hence, the concentration of dissolved oxygen is increased, and air and oxygen formed into finer bubbles are brought into contact with a surface of photocatalytic body fiber whereby the generation of the active oxygen species by the photocatalytic reaction can be performed more smoothly. At the same time, with the use of the ultrasonic wave oscillator, it is possible to easily allow electrons generated by the photocatalytic reaction which occurs on the photocatalytic body fiber to freely move.

Further, the active oxygen species which are generated on the photocatalytic fiber by these electrons are remarkably increased due to the high-speed movement (high-flow-rate movement) of water which flows on a surface of fiber due to the ultrasonic vibrations of the fibers and hence, it is possible to discharge the active oxygen species in water. That is, these ultrasonic waves accelerate the separation of the active oxygen species from the photocatalytic body and, at the same time, it is estimated that the ultrasonic waves and the ultra violet rays increase the reaction of active oxygen species due to an interaction between the ultrasonic waves and wavelengths of ultra violet rays.

Here, an ultrasonic oscillator for atomization which generates high frequency ultrasonic waves (generally 500 kHz or more) is used. Although the high-frequency ultrasonic-wave vibrations generated by the ultrasonic vibrator for atomization exhibits low fiber cleaning ability, the high-frequency ultrasonic-wave vibrations have power sufficient to shake off the electrons, the active oxygen species and the like generated by the photocatalytic reaction into water.

Further, the middle frequency ultrasonic waves (100 to 500 kHz) may be used as the ultrasonic waves used in this embodiment. With the use of the middle frequency ultrasonic waves, when the ultrasonic waves impinge on the fiber-like photocatalytic body, the diffraction of the ultrasonic waves is increased and hence, the agitation of water in the sealed container can be further strengthened whereby it is possible to efficiently separate the active oxygen species from the photocatalytic body. Further, due to an action of the middle frequency ultrasonic waves, it is possible to acquire effect of cleaning with respect to substances having comparatively large molecular weights such as stain components adhering to the fibers. However, the use ultrasonic waves of 100 kHz or less is not recommended because there is a possibility that such ultrasonic waves cause the deformation of the photocatalytic body or an peel-off damage on a photocatalytic reaction surface formed on the photocatalytic body.

Further, the means for diffusing the active oxygen species in water may be configured to mechanically move the photocatalytic body. Such a means can also allow water to efficiently contain the active oxygen species.

These ultrasonic waves can accelerate the separation of the active oxygen species from the photocatalytic body 20 and, at the same time, it is estimated that the ultrasonic waves and the ultra violet rays increase the reaction of active oxygen species due to an interaction between the ultrasonic waves and wavelengths of ultra violet rays.

In the apparatus for producing photocatalytic reaction water, upstream or downstream of a portion of the apparatus (for example, in the vicinity of the photocatalytic body) which generates a sterilization action by the photocatalytic reaction or at the same position as the apparatus, ultra violet rays having a wavelength of 254 to 265 nm may be radiated using a sterilizing lamp.

That is, water supplied to the photocatalytic body may be treated by the sterilizing lamp, water containing active oxygen obtained by the photocatalytic body may be treated by the sterilizing lamp, or the treatment by the sterilizing lamp may be performed in the vicinity of an area where the reaction of the photocatalytic body occurs.

In other words, by radiating ultra violet rays having a wavelength of 254 to 265 nm to the water which is brought into contact with the photocatalytic body, the photocatalytic reaction water or the water which is brought into contact with the photocatalyst, the cell membrane protein metamorphism is generated in microorganisms in respective water thus enhancing the sterilization effect on the microorganisms or bacteria in the produced photocatalytic reaction water and the parasites or protozoa elimination effect.

Originally, the cell membrane metamorphism of the microorganisms generated by the sterilizing lamp is considered to be the mutation disorder which occurs in DNA of the microorganisms due to the radiation of ultra violet rays. However, when the radiation of the ultra violet rays is interrupted, nucleic acid is recovered and regenerated, and so-called photo recovery is generated and hence, bacteria is regenerated and revived.

To further explain the mechanism of the action in detail, it has been known that the mutation disorder of DNA occurs particularly in a portion of the DNA where two pieces of thymine are continuously present in the same chain on a base sequence of the DNA.

That is, two carbons in a pyrimidine ring constituting thymine and two carbons in a pyrimidine ring of neighboring thymine are respectively bonded to each other due to energy of the ultra violet rays thus forming a rectangular cyclobutyl ring which constitutes a thymine dimer.

When the thymine dimer is present, the tertiary structure of the DNA is distorted and hence, when the DNA is replicated, the progress of replication forks of the DNA is prevented so that erroneous replication of DNA is easily generated. Further, upon reception of radiation of ultra violet rays to microorganisms, such a cyclobutyl ring is generated in every portion of the base sequence of the DNA and hence, it becomes difficult for the microorganisms to maintain suitable life activity. These reactions are well known as the ultra violet-ray-based disorder of the DNA and these reactions occur not only in water specifically but also in air. Further, to consider the influence on human body, these reactions are treated as pathogenesis of skin cancer and also are reported to cause turbidity in a crystalline lens or a cornea of an eye.

Here, with respect to the cyclobutyl ring generated on the DNA of the microorganisms due to the radiation of the ultra violet rays, there has been known that so-called photo recovery, a phenomenon in which the cyclobutyl ring is broken using energy of visible light due to PR enzyme (photo reactivating enzyme) which the microorganisms have so that the DNA is recovered occurs. When the photo recovery occurs, the thymine dimmer forming the cyclobutyl ring recovers two original thymines and hence, the microorganisms are revived and become continuously alive.

However, by supplying the bacterial cells which receive the DNA disorder or the weakened microorganisms to the apparatus for producing photocatalytic reaction water and by bringing them into contact with the active oxygen species generated by the photocatalytic body, the bacterial cells are oxidatively destructed thus giving fatal damages to the weakened microorganisms to surely sterilize the microorganisms in water.

Due to the use of the sterilizing lamp together with the apparatus for producing photocatalytic reaction water, the cell membranes of the disordered microorganisms receives the degeneration by oxidization by the photocatalytic reaction water and hence, also with respect to bacteria having strong cell membrane such as bacterial capsules, the cell membranes exhibit strong sterilization power whereby the nucleic acid disorder becomes permanent and cannot acquire the photo recovery.

Particularly, by constituting a circulation system in which the apparatus for producing photocatalytic reaction water is installed in a water reservoir or the like, it is possible to acquire more hygienic photocatalytic reaction water.

Further, the present invention is characterized in that water to be supplied to the photocatalytic body is produced by bringing at least one of oxygen, air and ozone into contact with water. Further, by using water having oxygen concentration thereof enhanced by bringing an oxygen generating agent into contact with water, it is possible to accelerate the photocatalytic reaction thus allowing water to efficiently contain the active oxygen species.

Here, the apparatus for producing photocatalytic reaction water according to the present invention exhibits a remarkable effect particularly in a field where it is necessary to sterilize the microorganisms, a field where it is necessary to eliminate parasites adhering to fish body and a field where it is necessary to eliminate protozoa such as amoeba. Accordingly, herein after, the application of the apparatus for producing photocatalytic reaction water is roughly classified into the application of the apparatus for producing photocatalytic reaction water to bacteria elimination, sterilization and cleaning and the application of the apparatus for producing photocatalytic reaction water to the elimination of protozoa, and the explanation is made with respect to the respective applications.

First of all, the explanation is made with respect to the apparatus for producing photocatalytic reaction water constituted for bacteria sterilization (herein after, also referred to as an apparatus for producing photocatalytic reaction water for bacteria sterilization).

Due to the apparatus for producing photocatalytic reaction water for sterilization, the bacteria sterilization and bacteria elimination can be performed by bringing microorganisms into contact with the produced photocatalytic reaction water and hence, the microorganisms can be effectively eliminated and sterilized.

The sterilization method is not particularly limited provided that the sterilization method can bring the microorganisms into contact with the photocatalytic reaction water. The sterilization may be performed in the following manner. That is, the microorganisms is supplied to the apparatus for producing photocatalytic reaction water for sterilization together with water, and the microorganisms are brought into contact with the active oxygen species in the inside of the device.

Further, by forming the apparatus for producing photocatalytic reaction water for eliminating parasites into a cleaning device which brings the produced water into contact with an object to be cleaned, the decomposition of organic substance can be performed in addition to the bacteria elimination and sterilization and hence, not to mention microorganism-level stains, naked-eye-level stains or the like can be removed.

As the object to be cleaned here, for example, an artificial teeth, medical equipment, tableware, vegetable, precision instrument, a toilet, cloth, rice seed and the like may be named. However, the object to be cleaned is not particularly limited to these objects.

Next, the explanation is made with respect to an apparatus for producing photocatalytic reaction water applicable to the elimination of parasites or protozoa (herein after, also referred to as an apparatus for producing photocatalytic reaction water for eliminating parasites or protozoa).

The an apparatus for producing photocatalytic reaction water according to the present invention is directed to the apparatus for producing photocatalytic reaction water for elimination of parasites or protozoa in which the active oxygen species generated due to the radiation of the light from the light source on the photocatalytic body is diffused in water thus imparting functions of active oxygen species to water thus eliminating fish parasites by making use of oxidation reaction using the water.

That is, in the same manner as the above-mentioned apparatus for producing photocatalytic reaction water for sterilization, the photocatalytic reaction water is brought into contact with the parasites thus performing elimination of parasites which adheres to or parasitize the fish.

Here, the water used in the apparatus for producing photocatalytic reaction water for eliminating parasites or protozoa is not particularly limited and, for example, fresh water, sea water, clear water or the like can be used.

The apparatus for producing photocatalytic reaction water for eliminating parasites or protozoa which can perform elimination of fish parasites may include a sterilizing lamp which can exhibit a sterilization effect.

Here, the apparatus for producing photocatalytic reaction water for eliminating parasites or protozoa which can perform the elimination of the fish parasites may be mounted on a container such as a water reservoir. Further, for example, assuming a fish preserve or the like as a large water reservoir, the whole fish preserve may be formed into an apparatus for producing photocatalytic reaction water for eliminating parasites or protozoa which can perform the elimination of fish parasites.

That is, according to the former example, the apparatus for producing photocatalytic reaction water for eliminating parasites or protozoa which can perform the elimination of the fish parasites is mounted on a water reservoir storing water and fish, for example, and water in the inside of the water reservoir is supplied to the apparatus for producing photocatalytic reaction water for eliminating parasites or protozoa, and water containing active oxygen species is returned to the water reservoir again. Accordingly, the water containing active oxygen species is brought into contact with the fish thus eliminating fish parasites.

Further, according to the latter example, for example, a sheet-like photocatalytic body is allowed to float on a fish preserve extended over sea water and the photocatalyst is excited by the sun light and, at the same time, the photocatalytic body is moved by a force of waves and hence, the active oxygen species generated in the photocatalytic body are diffused in sea water thus eliminating parasites adhering to fish body.

In this case, a shape of the photocatalytic body is not particularly limited, and the photocatalytic body may be configured such that an endless loop sheet body extends between and is wound around a drive roller and a driven roller and is rotatable so as to facilitate the inside-and-outside inversion of the sheet body.

By making use of the apparatus for producing photocatalytic reaction water for eliminating parasites or protozoa which can perform the elimination of the fish parasites according to the present invention, according to a method for eliminating parasites adhering to the fish, external parasites such as *Benedemia seriola* (*Lepeophtheirus salmonis, Benedenia seriolae, Benedenia skii, Neobenedenia girellae, Entobdella soleae* or the like) adhering to skin of fish body, or *Heteraxine heterocerca* (*Heterraxine Heterocerca, Zeuxapta japonica, Bivagina tai, Heterobothrium okamotoi, Heterobothrium tetrodonis, Neoheterobothrium hirame, Neoheterobothrium affine* or the like) adhering to a gill of fish body can be eliminated thus preventing or curing the fish sickness caused by these parasites.

At this time, by performing the elimination of the parasites while adjusting water temperature within ±5° C., favorably within ±3° C. from the cultivation environment water temperature of fish subjected to the parasite or protozoa elimination, it is possible to efficiently eliminate parasites without imposing stress attributed to temperature on fish.

Further, by adjusting water dissolved oxygen concentration to 12 mg/L or less, favorably to 10 mg/L or less, it is possible to enhance the contact efficiency between the photocatalytic body and the oxygen thus more effectively acquiring the parasites and protozoa elimination effect while preventing the fish subjected to the parasite or protozoa elimination from being weakened by the oxygen-based disorder.

Hereinafter, the explanation is made with respect to the present invention in further detail in conjunction with embodiments.

[Embodiment 1]

First of all, FIG. 1 shows an apparatus 1 for producing photocatalytic reaction water according to the present invention which can be used as an apparatus for producing photocatalytic reaction water for bacteria elimination as well as an apparatus for producing photocatalytic reaction water for parasite or protozoa elimination. A water reservoir 33 preliminarily stores water 31 therein, and water 31 is supplied to the apparatus 1 for producing photocatalytic reaction water through a water supply pipe 3 by driving a water supply pump 32 immersed in water 31.

Here, water 31 treated by the apparatus 1 for producing photocatalytic reaction water is turned into photocatalytic reaction water containing abundant active oxygen species and passes through the drain pipe 10, flows down from a drain opening 11 and returns to the water reservoir 33 again.

Figure 2:
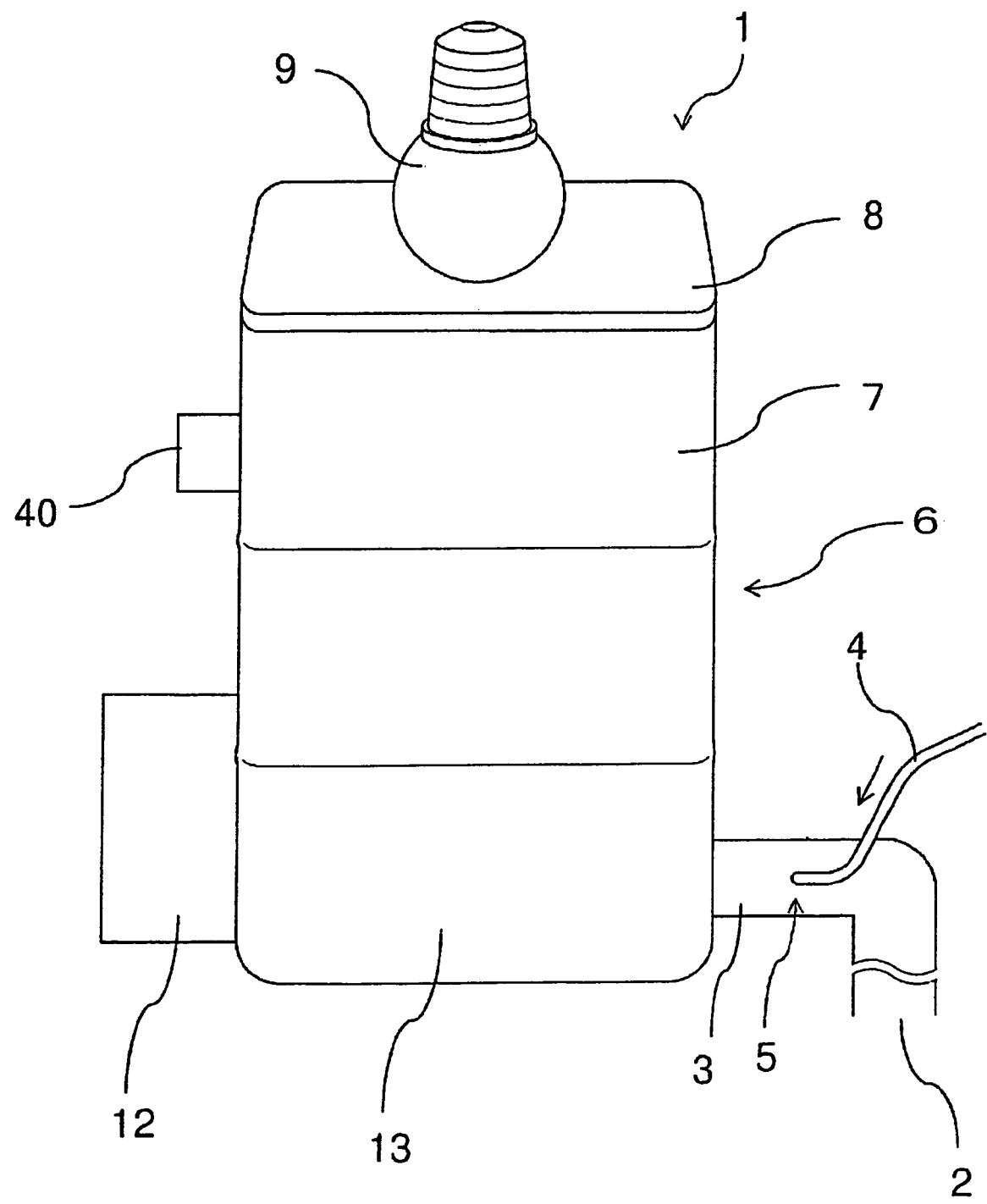
FIG. 2 is an appearance view of the apparatus for producing photocatalytic reaction water according to the present invention.
Figure 3:
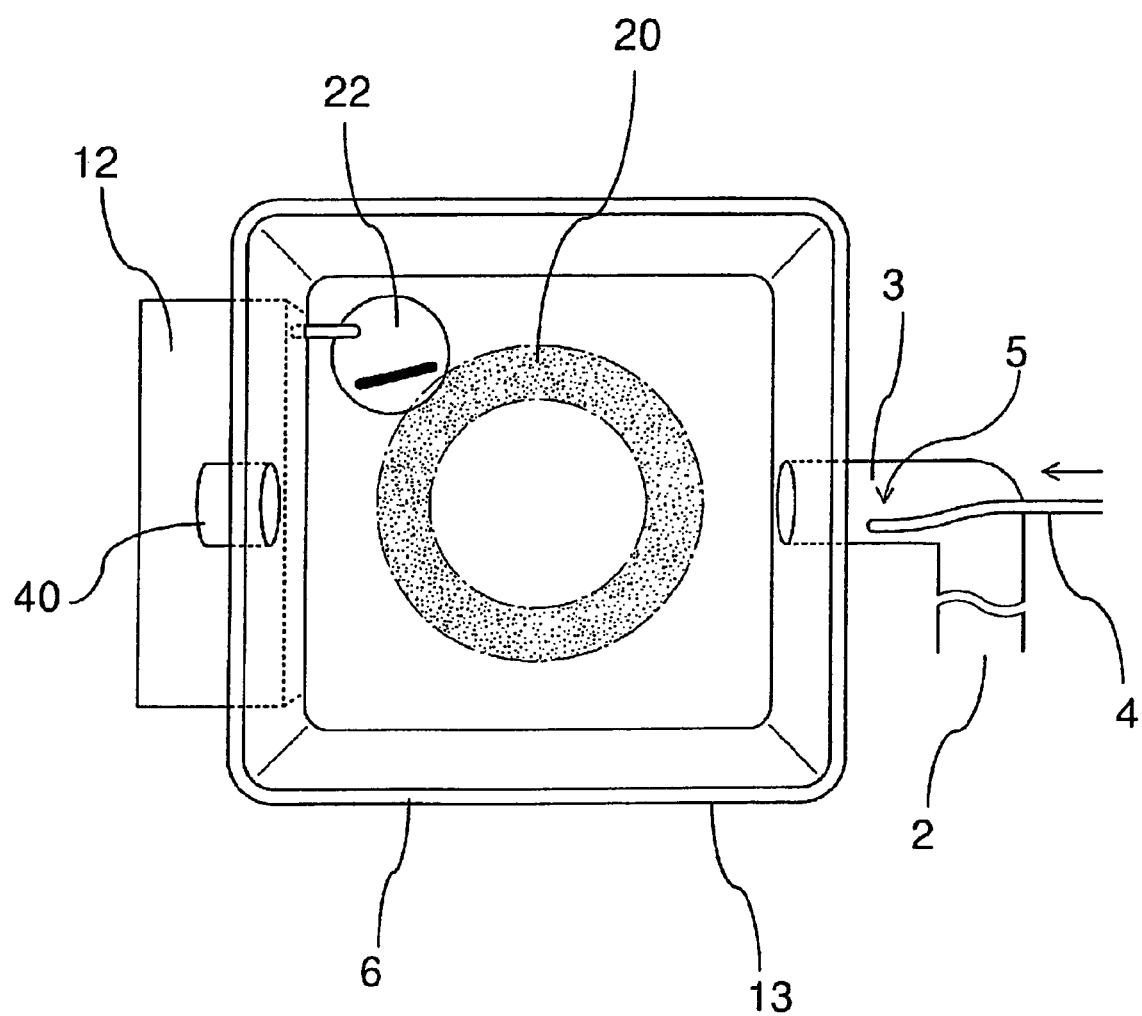
FIG. 3 is an explanatory view showing the inside of the apparatus for producing photocatalytic reaction water according to the present invention.
Figure 4:
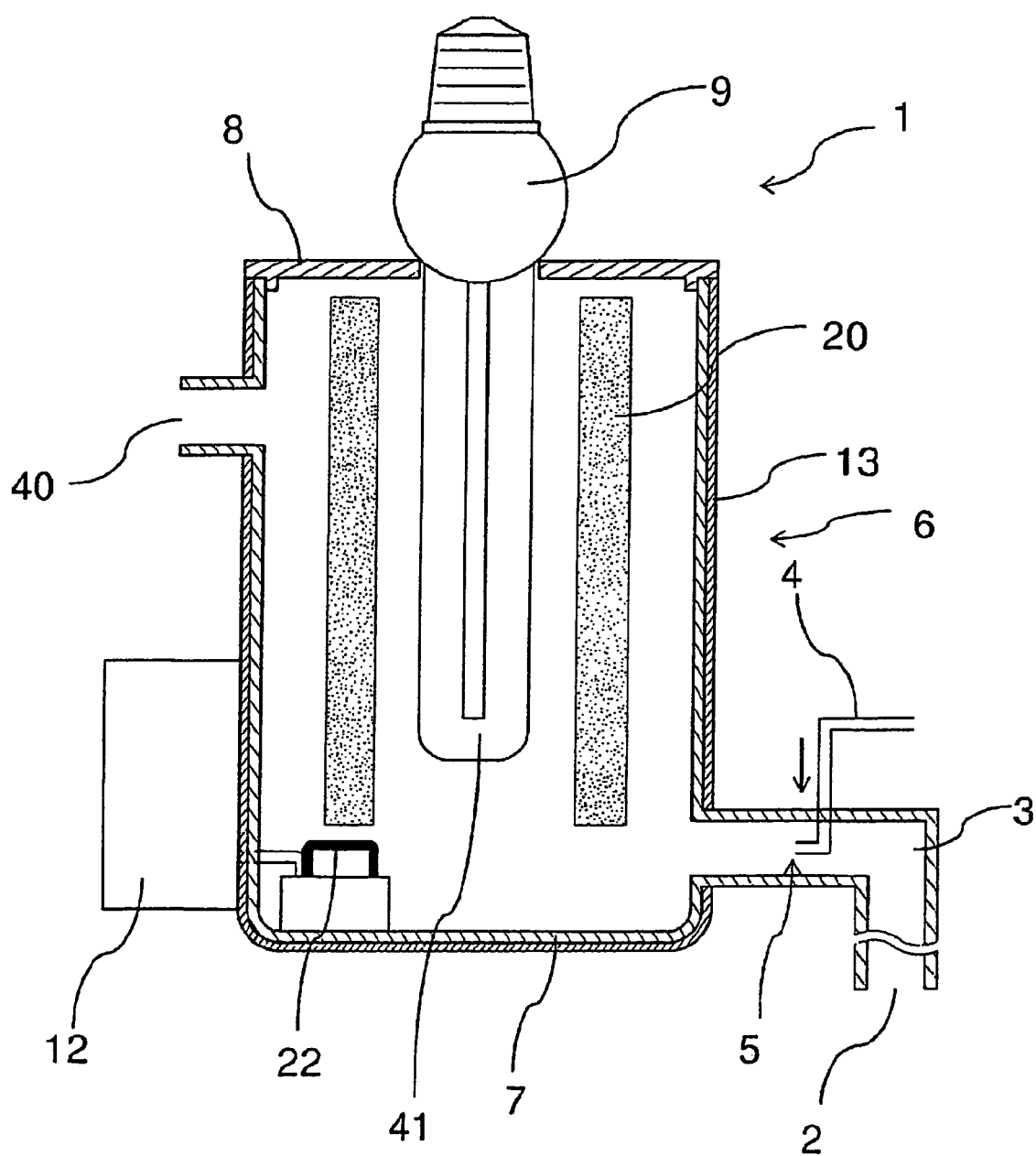
FIG. 4 is a cross-sectional view of the apparatus for producing photocatalytic reaction water according to the present invention.

Next, the explanation is made with respect to the more detailed constitution of the apparatus 1 for producing photocatalytic reaction water in conjunction with FIG. 2 to FIG. 4.

The apparatus 1 for producing photocatalytic reaction water includes, as shown in FIG. 2, a sealed container 6 constituted of a box-like container body 7 having an upper opening and a lid body 8 which closes the upper opening of the container body 7 in a sealing manner.

A material of the sealed container 6 is not particularly limited and may be made of metal, resin, plastic or the like. However, the sealed container 6 may preferably be made of a material difficult to be deteriorated by the radiation of ultra violet rays or a material having corrosion resistance difficult to be corroded by water or sea water. By forming the container body 7 and the lid body 8 using such a material, a lifetime of the apparatus 1 for producing photocatalytic reaction water can be increased. In the drawing, the sealed container 6 is made of plastic.

Further, a water discharge hose connection portion 40 for taking out the photocatalytic reaction water produced in the inside of the sealed container 6 is formed on an upper side surface of the container body 7. On the other hand, a water supply pipe 3 which extends outwardly is mounted on a lower side surface of the container body 7, and an opening end portion of the water supply pipe 3 constitutes a water supply opening 2 for supplying water to the inside of the sealed container 6. Here, in FIG. 1, a water supply pump 32 is connected to the water supply opening 2 for supplying water 31 into the apparatus 1 for producing photocatalytic reaction water. Here, in this embodiment, as the water supply pump 32, e-Roka PF-380 (flow rate: 6.2 L/min) is used.

Then, a hollow oxygen supply pipe 4 which allows the gas containing oxygen to pass therethrough is connected to a middle portion of the water supply pipe 3, and a connection portion constitutes an oxygen supply portion 5.

Here, a means for supplying oxygen to water is configured such that oxygen is efficiently diffused in water in a water current in the inside of the water supply pipe by connecting the oxygen supply pipe 4 to the water supply pipe 3. However, the oxygen supply means is not particularly limited provided that the oxygen supply means can allow water 31 supplied to the apparatus 1 for producing photocatalytic reaction water to contain oxygen. For example, the oxygen supply pipe 4 may be directly connected to the inside of the apparatus 1 for producing photocatalytic reaction water.

Further, the gas passing through the oxygen supply pipe 4 may be air or ozone, and may preferably be a gas having higher oxygen concentration. The higher the oxygen concentration supplied to the water, it is possible to allow water to efficiently contain oxygen and hence, a generation quantity of active oxygen species in the photocatalytic body can be increased.

Further, a method for enhancing the dissolved oxygen concentration in water 31 may use, for example, a foaming agent which reacts with water to form bubbles and allow the bubbles to generate oxygen therein.

On a lower side surface of the container body 7, an ultrasonic wave generator 12 which constitutes a diffusion means for diffusing active oxygen species in water is arranged. The ultrasonic wave generator 12 is connected to an ultrasonic wave oscillator 22 (2.4 MHz oscillator for atomization) arranged in the inside of the sealed container 6. Here, the ultrasonic wave oscillator which generates high frequency ultrasonic waves (generally considered to have frequency of 500 kHz or more) is used. However, ultrasonic waves having middle-frequency (100 kHz to 500 kHz) may be used.

It is estimated that these ultrasonic waves accelerate the separation of the active oxygen species from the photocatalytic body 20 and, at the same time, the reaction between the active oxygen species and the photocatalytic body 20 can be increased due to a mutual interference action between a wavelength of the ultrasonic waves and a wavelength of the ultra violet rays.

Further, in the embodiment 1, the active oxygen species are diffused by indirectly oscillating the photocatalytic body 20 by way of water 31 using ultrasonic waves as the diffusion means. However, the diffusion means of the active oxygen species is not limited to such a means. For example, the photocatalytic body 20 may be directly moved in the inside of the sealed container 6, or the active oxygen species may be diffused by arranging a fan (agitating blades) or the like which generates a water current by agitating water 31 in the sealed container 6.

An ultra violet ray lamp 9 (EFD15BLB made by Toshiba Lighting & Technology Corporation, peak wavelength: 352 nm, ultra violet ray output: 1.8 W) is inserted in the lid body 8 as a light source radiating light to the inside of the sealed container 6 in a state in which the ultra violet ray lamp 9 passes through the lid body 8. By supplying electricity to the ultra violet ray lamp 9, the ultra violet ray lamp 9 can radiate ultra violet rays to the photocatalytic body 20 described later provided to the inside of the sealed container 6. Further, since a current supply portion of the ultra violet ray lamp 9 is in air, even when a light emitting portion is immersed in water, there is no possibility of a trouble such as short-circuiting.

A blacklight or the like may be used as the ultra violet ray lamp 9. However, the ultra violet ray lamp 9 may be any ultra violet ray lamp provided that the ultra violet ray lamp 9 can effectively radiate ultra violet rays having a wavelength of 350 to 370 nm, and more favorably, a wavelength of 364 nm. The ultra violet ray lamp 9 is not particularly limited to the blacklight and an LED or a xenon lamp which can radiate ultra violet rays may be used as the ultra violet ray lamp 9. Further, when sun light is used as the light source, it is possible to radiate a large quantity of ultra violet rays contained in the sun light to the photocatalytic body. That is, it is possible to introduce light into water using optical fibers or an optical prism and to radiate light to the photocatalytic body 20. Further, provided that the photocatalytic body 20 is a rutile-type (visible-light-responsive-type) photocatalytic body, even normal visible rays (indoor illumination lamp) can generate a photocatalytic reaction and hence, it is possible to introduce light into water using optical fibers or an optical prism and to radiate the light to the photocatalytic body 20.

Next, FIG. 3 shows a state in which the lid body 8 is removed from the sealed container 6 and the inside of the container body 7 is viewed from the upper opening of the container body 7. FIG. 4 shows a cross section of the apparatus 1 for producing photocatalytic reaction water.

An ultrasonic wave oscillator 22 connected to the above-mentioned ultrasonic wave generator 12 is arranged on an inner-surface-side bottom portion of the container body 7 in a state in which the ultrasonic oscillator 22 is brought into contact with water. The cylindrical photocatalytic body 20 is arranged above the ultrasonic oscillator 22. The photocatalytic body 20 is, as shown in FIG. 4, arranged to surround a light emitting portion 41 of the ultra violet ray lamp 9 when the container body 7 is closed with the lid body 8. Accordingly, the ultra violet rays radiated by the ultra violet ray lamp 9 can be efficiently utilized as energy for exciting the photocatalytic body 20.

Here, the ultra violet rays radiated from the ultra violet ray lamp 9 and pass through the photocatalytic body 20 impinge on the container body 7 and the lid body 8.

Here, outer peripheral surfaces of the container body and the lid body 8 are covered with a reflector 13 which can reflect light such as ultra violet rays.

Accordingly, ultra violet rays which arrive at the container body 7 and the lid body 8 are reflected toward the inside of the container body 7 (that is, the direction of the photocatalytic body 20) by the reflector 13 and excite the photocatalytic body 20 and hence, the ultra violet rays radiated from the ultra violet ray lamp 9 can be utilized as activation energy of the photocatalytic body 20 without wasting the energy of the ultra violet rays.

The reflector 13 may preferably be made of a material which can reflect light, particularly, a material which can reflect ultra violet rays. For example, the reflector 13 may be made of aluminum foil.

Further, in the embodiment, the reflector 13 is adhered to outer peripheral surfaces of the container body 7 and the lid body 8. However, the reflector 13 may be adhered to the inner peripheral surfaces of the container body 7 and the lid body 8, or the sealed container per se may be made of a material having a similar function as the reflector 13. Particularly, when the sealed container 6 is made of plastic or resin, by forming the reflector 13 on an inner wall of the sealed container 6, a quantity of the ultra violet rays which is received by the sealed container 6 can be reduced and hence, the deterioration or the degeneration of plastic or resin attributed to the ultra violet rays can be prevented.

Further, the photocatalytic body 20 is formed by applying a titania thin film to substantially whole surface of the alumina metal fiber body by coating. By receiving the ultra violet rays radiated from the ultra violet ray lamp 9, the titania thin film can be excited.

Here, in the embodiment 1, the carrier of photocatalyst (titania) is formed of a metal-made fiber body. However, the carrier is not limited to the metal-made fiber body, and the carrier of photocatalyst can be formed of a porous body constituted of an organic and/or inorganic material. For example, the photocatalytic body 20 may be formed by applying a titania thin film to a surface of a glass fiber body, a ceramic fiber body or an non-woven cloth. Here, the porous body is a concept including a wooly object which is an aggregation of fiber bodies.

Next, the explanation is made herein after with respect to a flow of water supplied from the water supply opening 2 from a point of time that water contains the active oxygen species to a point of time that water is taken out from the drain opening 11.

That is, water 31 supplied from the water supply opening 2 flows through the water supply pipe 3 and reaches the oxygen supply portion 5. The oxygen supply pipe 4 is connected to the oxygen supply portion 5, and water 31 which arrives at the oxygen supply portion 5 is mixed with oxygen fed through the oxygen supply pipe 4.

Oxygen mixed with water 31 in this manner is dissolved in water 31 thus increasing the concentration of dissolved oxygen in water, becomes fine bubbles, and is fed to the inside of the sealed container 6. The bubbles which arrive at the inside of the sealed container 6 are formed into further minute bubbles due to the ultrasonic wave oscillation thus further increasing the concentration of dissolved oxygen in water 31. Further, remaining minute bubbles impinge on the photocatalytic body 20 and pop to generate high frequency ultrasonic waves. The ultrasonic waves directly or indirectly oscillate the photocatalytic body 20 thus facilitating the acceleration of the separation of the active oxygen species.

Water 31 in which the concentration of dissolved oxygen is increased arrives at the inside of the sealed container 6 and is filled in the sealed container 6.

On the other hand, ultra violet rays having a wavelength of 350 to 370 nm are radiated from the ultra violet ray lamp 9 to which electricity is supplied, and the radiated ultra violet rays impinge on the photocatalytic body 20 surrounding the ultra violet ray lamp 9.

Since the titania thin film having photocatalytic property is formed on the surface of the photocatalytic body 20, due to the impingement of the ultra violet rays radiated from the ultra violet ray lamp 9 on the titania thin film, the titania thin film is excited thus activating the photocatalytic body 20.

Since the energy (hv) of the ultra violet rays radiated from the ultra violet ray lamp 9 excites titania ($TiO_2$) constituting the titania thin film on the surface of the activated photocatalytic body 20, by bringing water 31 filled in the sealed container 6 into contact with the excited photocatalytic body 20, the active oxygen species are generated.

Further, water 31 filled in the sealed container 6 assumes a state in which the concentration of dissolved oxygen is high due to the oxygen admixed in the oxygen supply portion 5 and hence, it is possible to enhance the efficiency in bringing electrons ($e^-$) generated on the photocatalytic body 20 and the oxygen contained in water 31 into contact with each other.

Accordingly, water 31 containing a large quantity of oxygen is brought into contact with the activated photocatalytic body 20 and hence, the photocatalytic reaction vigorously occurs, and a larger quantity of active oxygen species is generated on the surface of the photocatalytic body 20.

Further, fine bubbles generated at the time of mixing oxygen into water 31 crack due to the impingement of the bubbles on the metal fiber body thus generating ultrasonic waves, and the metal fiber body is oscillated by the ultrasonic waves. Accordingly, the active oxygen species generated on the metal fiber body is easily discharged from the metal fiber body.

On the other hand, the ultrasonic wave generator 12 to which electricity is supplied oscillates the ultrasonic oscillator 22 arranged in the inside of the sealed container 6 thus generating ultrasonic waves.

Here, the generated ultrasonic waves oscillate water 31 and the photocatalytic body 20. Particularly, the photocatalytic body 20 installed in the apparatus 1 for producing photocatalytic reaction water according to the present invention is formed of the metal-made fiber body which is obtained by applying a photocatalyst (for example, titania) to a surface of metal-made fibers by coating and by forming the photocatalyst-coated metal-made fibers into a wooly aggregate.

Accordingly, simultaneously with the generation of the active oxygen species from the surface of the metal-made fiber body having a large surface area obtained by aggregating surface areas of the respective metal-made fibers, the generated active oxygen species are smoothly sieved from the surface of the photocatalytic body 20 due to the oscillations of the ultrasonic waves and hence, a large quantity of active oxygen species floats in water 31.

Further, new active oxygen species are immediately generated on the surface of the photocatalytic body 20, and these active oxygen species are sieved from the surface of the photocatalytic body 20 again along with the oscillations of the ultrasonic waves, and floats in water 31 again.

The above-mentioned reaction is carried out momentarily and is repeated many times and hence, it is possible to extremely efficiently allow water 31 to contain the active oxygen species therein.

Further, the photocatalytic body 20 can be more easily oscillated along with the fine oscillations of the ultrasonic waves compared to a plate-like photocatalyst and hence, it is possible to easily separate the active oxygen species from the surface of the photocatalytic body 20.

Further, distal end portions of a large number of metal-made fibers which presents in the photocatalytic body 20 acts as free ends under the ultrasonic oscillations and hence, it is possible to efficiently sieve the active oxygen species from the photocatalytic body 20.

Further, the photocatalytic body 20 preferably adopts alumina fibers which enable favorable coating of titania as a carrier thereof and hence, titania is relatively fixedly bonded to a surface of alumina whereby the photocatalytic body 20 exhibits high durability. Accordingly, the photocatalytic body 20 can withstand the long-time use while maintaining the practicality even in water under the ultrasonic-wave environment. Particularly, the above-mentioned high practicality of the photocatalytic body 20 is remarkably recognized when the photocatalytic body 20 is used in sea water which easily corrodes metal or the like.

As described above, due to the synergistic effect of the characteristic of the photocatalytic body 20 and the ultrasonic waves, the active oxygen species generated on the surface of the photocatalytic body 20 can easily separated into water and hence, a large quantity of active oxygen species is contained in water thus producing photocatalytic reaction water.

Further, due to water 31 continuously supplied from the water supply opening 2, photocatalytic reaction water in the sealed container 6 is pushed out from the drain opening 11 formed in an upper side surface of the sealed container 6 and hence, it is possible to take out the photocatalytic reaction water from the inside of the sealed container 6.

The active oxygen species contained in photocatalytic reaction water produced as described above exhibits the extremely high reactivity and can maintain the reactivity for a long time and hence, it is possible to readily give a fatal effect to the microorganisms or the parasites due to the strong oxidization decomposition ability of the active oxygen species.

[Embodiment 2]

Next, the explanation is made with respect to a case that the apparatus 1 for producing photocatalytic reaction water described in the embodiment 1 is used as an apparatus for producing photocatalytic reaction water for eliminating bacteria.

Figure 5:
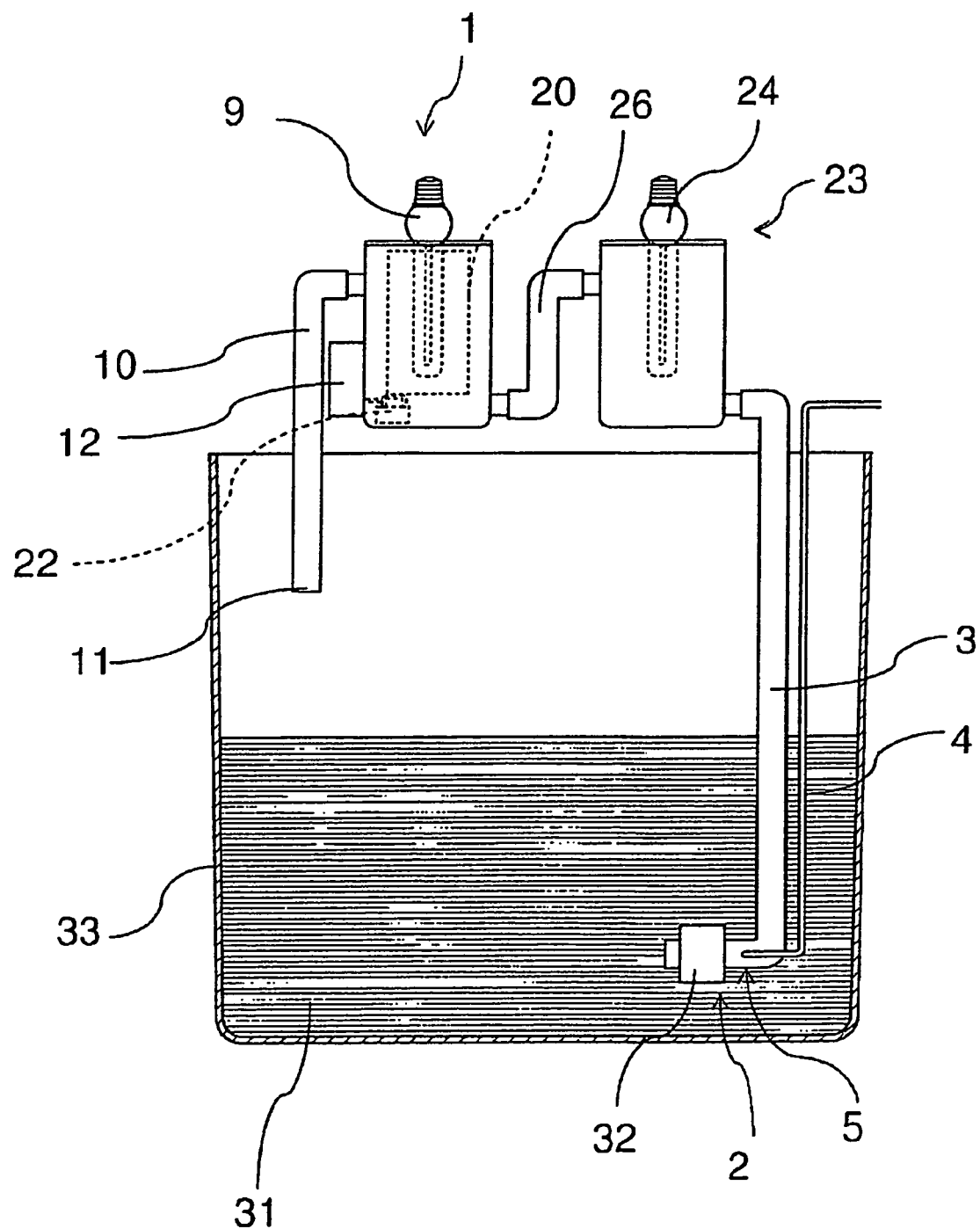
FIG. 5 is an explanatory view of the apparatus for producing photocatalytic reaction water for eliminating microorganisms according to an embodiment of the present invention.

That is, as shown in FIG. 5, between a water supply pump 32 immersed in water 31 stored in a water reservoir 33 and the apparatus 1 for producing photocatalytic reaction water, a sterilizer 23 including a sterilizing lamp 24 is arranged. Ultra violet rays radiated from the sterilizing lamp 24 can be radiated to water 31 which circulates in the inside of the sterilizer 23.

A sterilizing lamp 24 mounted on the sterilizer 23 can radiate ultra violet rays having a wavelength of 245 to 265 nm, and more preferably, a wavelength of 256 nm, and the sterilizing lamp 24 can sterilize the microorganisms by giving damages attributed to the mutation disorder to DNA of the microorganisms in water.

Further, a mirror surface formed on a wall surface of the apparatus 1 for producing photocatalytic reaction water and a pipe to which light blocking treatment is applied also possess an effect of preventing the recovery of bacteria by receiving light. By preventing the photo recovery, that is, the recovery of bacteria by receiving light, it is possible to efficiently give the damages attributed to the ultra violet rays having a wavelength of 245 to 265 nm to the microorganisms thus enhancing the sterilization effect.

In this apparatus 1 for producing photocatalytic reaction water, the active oxygen species and the like are diffused in water and hence, the microorganisms which are weakened by receiving the damage of cell membrane without being sterilized by the sterilizer 23 arrive at the apparatus 1 for producing photocatalytic reaction water whereby the microorganisms receive a further fatal damage by the active oxygen species leading to the further sterilization of the microorganisms.

Here, although the sterilizer 23 is arranged on the apparatus 1 for producing photocatalytic reaction water by way of a connection pipe 26, the arrangement structure of the sterilizer 23 is not limited to the above-mentioned arrangement structure. The apparatus 1 for producing photocatalytic reaction water and the sterilizer 23 may be integrally formed such that the sterilizing lamp 24 which generates ultra violet rays having a wavelength of 245 to 265 nm is arranged in the inside of the apparatus 1 for producing photocatalytic reaction water together with a light source (for example, an ultra violet ray lamp 9 generating ultra violet rays having a wavelength of 350 to 370 nm) for exciting the photocatalytic body 20 arranged in the inside of the sterilize-use apparatus 1 for producing photocatalytic reaction water. Further, there may be a case that a light source which radiates light for exciting the photocatalytic body 20 simultaneously with light for sterilizing microorganisms is arranged in the inside of the apparatus 1 for producing photocatalytic reaction water.

[Embodiment 3]

Next, the explanation is made with respect to an example in which the sterilization of the microorganisms is actually performed by making use of the apparatus 1 for producing photocatalytic reaction water according to the present invention.

In this embodiment, five kinds of tests are performed while changing the constitution of the apparatus 1 for producing photocatalytic reaction water and an operation time for every test, and results of the respective tests are studied. Contents of the respective tests are explained as follows.

[Test 1] Verification of bacteria elimination/sterilization ability of photocatalytic reaction water (no supply of oxygen and no radiation of ultrasonic waves)

[Test 2] Verification of bacteria elimination/sterilization effect when ultra violet rays having different wavelengths are radiated to the photocatalytic body 20 (no supply of oxygen and no radiation of ultrasonic waves)

[Test 3] Verification of bacteria elimination/sterilization effect when the supply of oxygen is performed simultaneously with the radiation of ultrasonic waves

[Test 4] Verification of duration of bacteria elimination/sterilization ability of photocatalytic reaction water

[Test 5] Verification of bacteria elimination/sterilization effect when the sterilizer is used together with the apparatus 1 for producing photocatalytic reaction water Hereinafter, the above-mentioned tests 1 to 5 are explained in detail.

[Test 1] Verification of Bacteria Elimination/Sterilization Ability of Photocatalytic Reaction Water Bacterial strains of five viable bacteria consisting of *Staphylococcus aureus*, *Enterococcus faecalis*, *Bacillus cereus*, *Escherichia coli*, and *Klebsiella pneumoniae* are suspended in water stored in the water reservoir 33 of the apparatus 1 for producing photocatalytic reaction water having the constitution shown in FIG. 1 (here, no supply of oxygen and no radiation of ultrasonic waves), and the concentration of bacteria is adjusted to substantially $10^6$ cfu/ml.

Figure 6:
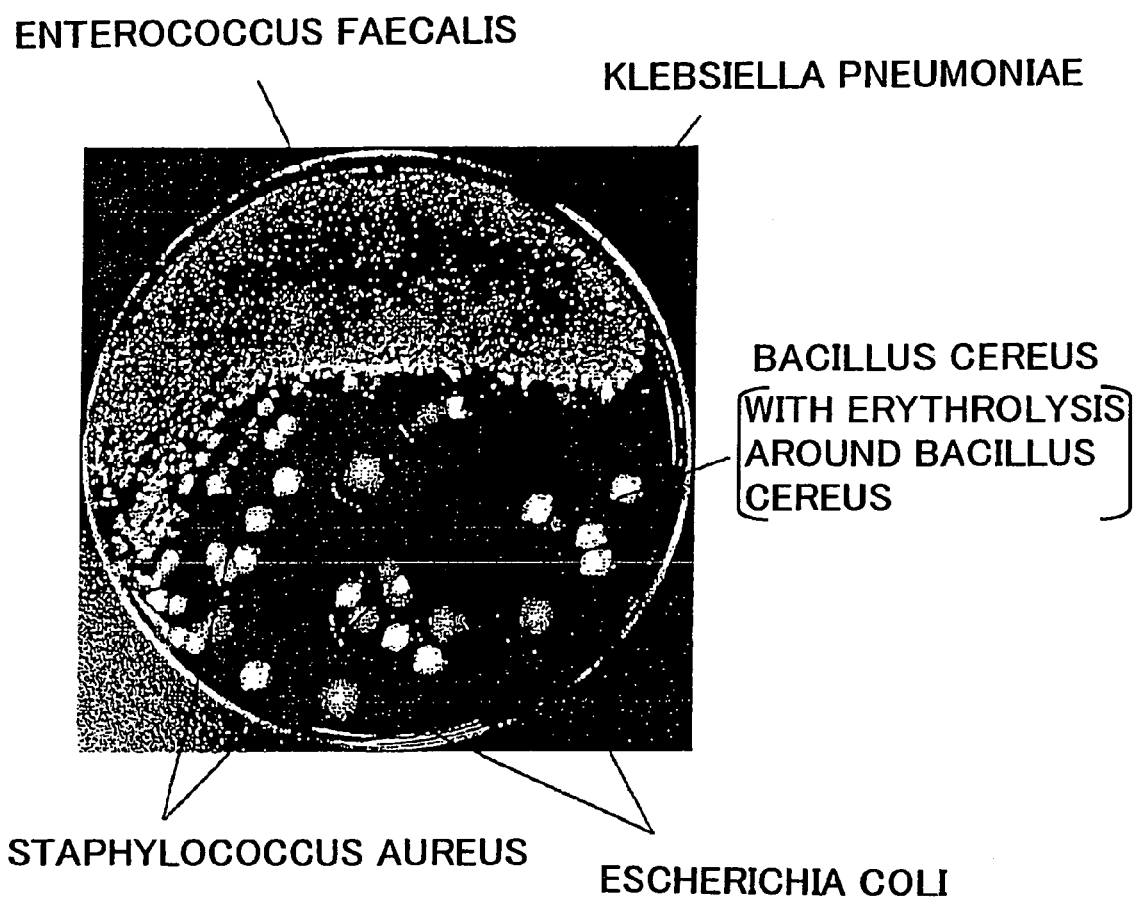
FIG. 6 is an explanatory view of a microorganism which forms a colony on an agar medium.

In the apparatus 1 for producing photocatalytic reaction water having such constitution, electricity is supplied to the underwater pump 32 and the blacklight 9 (EFD15BLB made in TOSHIBA LIGHTING & TECHNOLOGY CORP) so as to circulate water for three hours, and a change of number of viable bacteria with time is observed. Here, with respect to water used in this test, distilled water for injection 4 L is adopted. The apparatus for producing photocatalytic reaction water, the circuit and the underwater pump are preliminarily sterilized and are subject to circulation cleaning using distilled water. Water is circulated with no change of water temperature during the experiment. That is, water is circulated while keeping a fixed temperature of 28° C. FIG. 6 shows states of bacterial strains of five bacteria on an agar medium.

Figure 7:
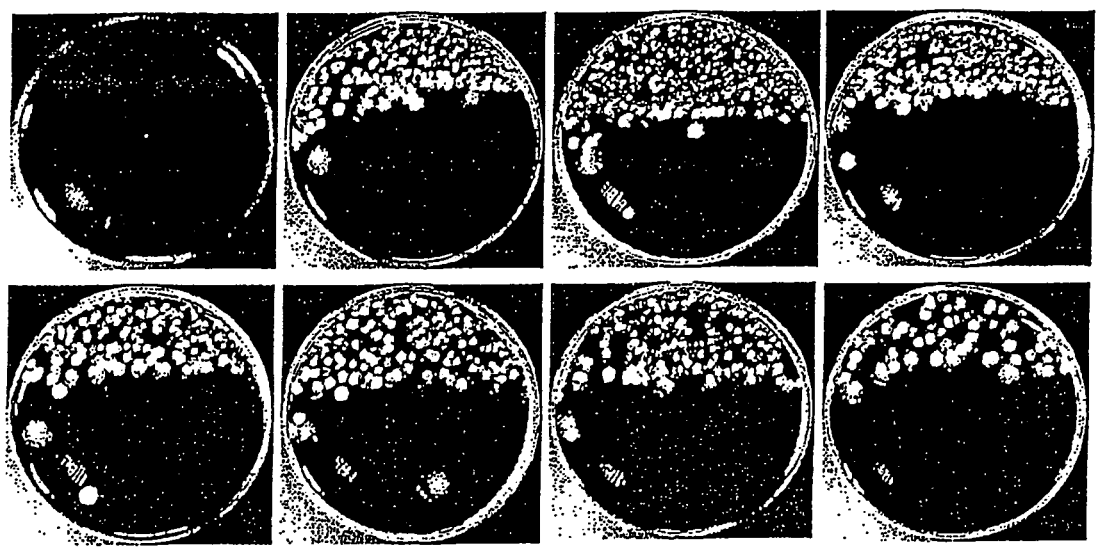
FIG. 7 is an explanatory view of a microorganism which forms a colony on an agar medium.

The research of the number of viable bacteria is made by scattering specimens which are sampled with time on a blood agar medium (trypticasesoy blood agar) and by observing the growth of the specimens. Further, to observe gram-positive bacteria more easily, a blood agar medium (COLUMBIA BLOOD AGAR) to which CAN (Collistin-Nalidixic Acid; medicinal for suppressing gram-negative *bacillus*) is used. FIG. 7 shows a change with time of colonies formed on the blood agar medium as described above.

From a result shown in FIG. 7, it is understood that photocatalytic reaction water exhibits a remarkable bacteria elimination/control effect for all of five bacterial strains of bacteria suspended in water. The bacteria grow spending thirty minutes from a point of time the bacteria are supplied into water and, thereafter, the number of viable bacteria thereof is decreased with time. Particularly, *Enterococcus faecalis* is almost exterminated at a point of time that three hours has lapsed.

According to a result of this test 1, it is confirmed that the apparatus 1 for producing photocatalytic reaction water exhibits the bacteria elimination/sterilization effect. At this point of time, however, it is considered that, the active oxygen species generated by the photocatalyst merely acts on the surface of the photocatalytic body and the sterilization effect appears by bringing the photocatalytic body into contact with the bacteria frequently due to the circulation of water in the inside of the water reservoir. Accordingly, as the determination at this point of time, it is difficult to determine whether or not photocatalytic reaction water generated by the apparatus 1 for producing photocatalytic reaction water have the bacteria elimination/sterilization effect.

[Test 2] Verification of Bacteria Elimination/Sterilization Effect when Ultra Violet Rays Having Different Wavelengths are Radiated to the Photocatalytic Body 20:

Next, in the test having the substantially same test system as test 1, the verification of bacteria elimination/sterilization effect is performed with respect to a case that ultra violet rays having different wavelengths from ultra violet rays used in test 1 are radiated to the photocatalytic body 20.

That is, in test 2, the ultra violet ray radiation lamp mounted on the apparatus 1 for producing photocatalytic reaction water used in test 1 is replaced with a black lamp which radiates blue rays hardly radiating ultra violet rays effective for the titania fiber body, and the change of number of bacteria is observed. Here, there is no change of water temperature. That is, water is circulated at a fixed water temperature of 28° C.

As a result, the number of bacteria is steadily and relatively gently increased immediately after starting the test. After a lapse of 45 minutes, concentrations of all bacterial strains exceed $10^8$ cfu/ml, and the respective states of the bacterial strains are no more observed. Usually, a growth rate of the bacteria is considered to be doubled in 20 minutes. In the result of test 2, a bacteria control effect is also not confirmed. Accordingly, it is confirmed that the photocatalytic body arranged in the inside of the apparatus 1 for producing photocatalytic reaction water does not have the bacteria elimination/sterilization action.

As described above, according to the results of the test 1 and the test 2, it is confirmed that the apparatus 1 for producing photocatalytic reaction water generates the bacteria elimination/sterilization effect attributed to the photocatalytic reaction, and that the bacteria elimination/sterilization effect is not attributed to the photocatalytic body per se.

However, it is considered that the reaction ability is not sufficient to completely eliminate the viable bacteria in the inside of water, and some auxiliary means becomes necessary.

[Test 3] Verification of Bacteria Elimination/Sterilization Effect when the Supply of Oxygen and the Radiation of Ultrasonic Waves are Performed Simultaneously:

Next, five bacterial strains of viable bacteria consisting of *Staphylococcus aureus, Enterococcus faecalis, Bacillus cereus, Escherichia coli*, and *Pseudomonas aeruginosa* are suspended in water stored in the water reservoir 33 of the sterilize-use apparatus 1 for producing photocatalytic reaction water having the constitution shown in FIG. 1. The concentration of the bacteria is adjusted to substantially $10^6$ cfu/ml.

In the system having such a constitution, electricity is supplied to the underwater pump 32, the blacklight 9 (EFD15BLB made in TOSHIBA LIGHTING & TECHNOLOGY CORP) and the ultrasonic oscillator 12 (oscillator for atomization of 2.4 MHz) so as to circulate water for 24 hours while feeding pure oxygen into water from the oxygen supply portion 5 at a flow rate of 250 ml/min, and a change of number of viable bacteria with time is observed. Further, the test 3 is performed using a protocol substantially equal to a protocol for the test 1, and the change of the number of bacteria is observed by measuring the number of viable bacteria by diluting water stored in the water reservoir 33 taken out from the water reservoir 33 for every fixed time by a spiral-plater in stages. Further, in the substantially same manner as the test 1, there is no change of water temperature during an experiment. That is, water is circulated at a fixed temperature of 28° C.

A result of the test 3 is shown in Table 1.

TABLE 1

| | 0 minute | 30 minutes | 60 minutes | 120 minutes | 180 minutes | 240 minutes |
|---|---|---|---|---|---|---|
| *Staphylococcus aureus* (MRSA) | $6.0 \times 10^5$ | 0 | 0 | 0 | 0 | 0 |
| *Enterococcus faecalis* | $4.0 \times 10^6$ | $1.0 \times 10^4$ | $1.0 \times 10^4$ | $2.0 \times 10^3$ | $1.0 \times 10^3$ | $2.0 \times 10^3$ |
| *Bacillus cereus* | $6.0 \times 10^2$ | 0 | 0 | 0 | 0 | 0 |
| *Escherichia coli* | $2.0 \times 10^5$ | $4.0 \times 10^3$ | 0 | 0 | 0 | 0 |
| *Pseudomonas aeruginosa* | $6.0 \times 10^5$ | $2.0 \times 10^4$ | $4.0 \times 10^4$ | $1.0 \times 10^4$ | $1.0 \times 10^3$ | $9.0 \times 10^2$ |
| Gram Negative Rod | 0 | 0 | 0 | 0 | 0 | 0 |

| | 360 minutes | 540 minutes | 720 minutes | 960 minutes | 1200 minutes | 1440 minutes |
|---|---|---|---|---|---|---|
| *Staphylococcus aureus* (MRSA) | 0 | 0 | 0 | 0 | 0 | 0 |
| *Enterococcus faecalis* | 0 | 0 | 0 | 0 | 0 | 0 |
| *Bacillus cereus* | 0 | 0 | 0 | 0 | 0 | 0 |
| *Escherichia coli* | 0 | 0 | 0 | 0 | 0 | 0 |
| *Pseudomonas aeruginosa* | $6.0 \times 10^2$ | $1.0 \times 10^3$ | $2.0 \times 10^3$ | $4.0 \times 10^3$ | $2.0 \times 10^4$ | $1.0 \times 10^6$ |
| Gram Negative Rod | $1.0 \times 10^2$ | $1.0 \times 10^3$ | $2.0 \times 10^4$ | $1.0 \times 10^6$ | $2.0 \times 10^6$ | $3.0 \times 10^6$ |

Unit: cfu/ml

As can be understood from Table 1, the remarkable bacteria elimination/sterilization effect is observed for four bacterial strains suspended in water. Particularly, *Staphylococcus aureus* which acquires the antibiotic resistance and causes the hospital infection and *Bacillus cereus* which causes the food poisoning die out within one hour after staring the test and hence, it is confirmed that by performing the radiation of ultrasonic waves and the supply of oxygen, a high bacteria elimination/sterilization effect can be acquired against these bacteria. Further, although it has been considered that *Bacillus cereus* is spore bacteria so that it is difficult to exterminate the *Bacillus cereus*, this test suggests that the sterilization effect is effectively observed also against the spore bacteria.

In addition, it is also found that *Escherichia coli* to which pathogenic *Escherichia coli* 0-157 or the like belongs speedily dies out, and no re-propagation of the *Escherichia coli* is observed.

On the other hand, with respect to *Pseudomonas aeruginosa*, although the decrease of the number of bacteria is once observed, thereafter, a phenomenon that the number of bacteria is gradually increased is observed. Further, also with respect to the gram-negative bacteria with a thick cell membrane having a bacterial capsule which is mixed into the test system, the tendency that the number of bacteria is gradually increased is observed.

As described above, it is found that, due to the synergistic effect of the oxygen injection and the ultrasonic wave oscillations, photocatalytic reaction water can obtain a strong sterilizing power against *Staphylococcus aureus, Enterococcus faecalis, Bacillus cereus,* and *Escherichia coli*. It is also found that photocatalytic reaction water can obtain a bacteria control force for suppressing the propagation of bacteria with respect to *Pseudomonas aeruginosa* and gram-negative bacteria.

[Test 4] Verification of Duration of Bacteria Elimination/Sterilization Ability of Photocatalytic Reaction Water:

Next, to verify the duration of the sterilization effect of photocatalytic reaction water, the apparatus 1 for producing photocatalytic reaction water is stopped after operating the apparatus 1 for 1 hour, bacteria is suspended in water stored in the water reservoir 33, and a reaction continuation time is estimated by observing the change of the number of bacteria with time.

Also in this test 4, in the same manner as the test 3, the apparatus 1 for producing photocatalytic reaction water is arranged in the water reservoir 33, and concentrations of four bacterial strains of viable bacteria consisting of *Staphylococcus aureus, Enterococcus faecalis, Escherichia coli,* and *Pseudomonas aeruginosa* are adjusted to approximately $10^6$ cfu/ml. A result of the test 4 is shown in Table 2.

TABLE 2

|  | 0 minute | 0 minute | 15 minutes | 30 minutes | 45 minutes | 60 minutes | 90 minutes | 120 minutes |
|---|---|---|---|---|---|---|---|---|
| *Staphylococcus aureus* (MRSA) | 0 | 0 | $3 \times 10^2$ | $2 \times 10^4$ | 0 | 0 | 0 | 0 |
| *Enterococcus faecalis* | 0 | 0 | $3 \times 10^1$ | $3 \times 10^7$ | $3 \times 10^4$ | $2 \times 10^2$ | 0 | 0 |
| *Escherichia coli* | 0 | 0 | $3 \times 10^1$ | 0 | 0 | 0 | 0 | 0 |
| *Pseudomonas aeruginosa* | 0 | 0 | $3 \times 10^2$ | $2 \times 10^2$ | $3 \times 10^2$ | 0 | 0 | 0 |

As can be understood from Table 2, although an action of photocatalytic reaction water differs among the bacterial strains, it is found that the action of photocatalytic reaction water continues for substantially 1 hour.

In this experiment, the photocatalytic reaction is not generated during a time that bacteria circulate. A sterilization action is caused by the photocatalytic reaction water produced by operating the apparatus 1 for producing photocatalytic reaction water for 1 hour. Accordingly, it is found that the photocatalytic reaction water has the strong sterilization ability and the possibility that the sterilization action continues for substantially 1 hour is recognized.

[Experiment 5] Verification of Bacteria Elimination and Sterilization Effect when Sterilizer 23 is Used Together with Apparatus for Producing Photocatalytic Reaction Water Next, in the apparatus 1 for producing photocatalytic reaction water which performs the supply of oxygen and the radiation of ultrasonic waves, an experiment is performed with respect to the behavior of microorganisms when a blacklight is further used, that is, when ultra violet rays are further radiated.

As bacteria used in this experiment 5, in the same manner as the experiment 4, four kinds of viable bacteria, that is, *Staphylococcus aureus, Enterococcus faecalis, Escherichia coli, Pseudomonas aeruginosa* are suspended in water stored in the water reservoir 33. While operating the underwater pump 32 for 1 hour after starting the experiment, the supply of oxygen and the radiation of ultrasonic waves are performed. At this point of time, the photocatalytic reaction is not generated and hence, the bacteria supplied to the inside of the circuit can recover from damages caused by preservation and can propagate. Next, after a lapse of one hour, the blacklight is turned on while the above-mentioned state is maintained so as to excite the photocatalytic reaction in the photocatalytic body 20, and the bacteria elimination effect and the sterilization effect caused by the photocatalytic reaction are observed for 3 hours. Then, after a lapse of 180 minutes from starting of the experiment, the sterilizing lamp 24 of the sterilizer 23 is turned on and an additional effect acquired by the sterilizer 23 is confirmed. Table 3 shows a result of a search of change of the number of respective viable bacteria with time in the experiment 5.

TABLE 3

| | | Oxygen & supersonicwave → | | | | | | | | | | | | | | | | | |
| | | | | Black light (peak 352 nm) → | | | | | | | | | | | | | | | |
| | | | | | | | | | | Sterilizing lump (peak 256 nm) → | | | | | | | | | |
| | 0 minute | 30 minutes | 60 minutes | 65 minutes | 70 minutes | 75 minutes | 90 minutes | 105 minutes | 120 minutes | 150 minutes | 180 minutes | 240 minutes | 255 minutes | 270 minutes | 285 minutes | 300 minutes | 330 minutes | 360 minutes | 420 minutes |
|---|---|---|---|---|---|---|---|---|---|---|---|---|---|---|---|---|---|---|---|
| *Staphylococcus aureus* (MRSA) | 0 | $4 \times 10^1$ | $3 \times 10^3$ | $3 \times 10^3$ | $2 \times 10^5$ | $2 \times 10^2$ | $1 \times 10^8$ | 0 | 0 | 0 | 0 | 0 | 0 | 0 | 0 | 0 | 0 | 0 | 0 |
| *Enterococcus faecalis* | 0 | $4 \times 10^2$ | $3 \times 10^9$ | $4 \times 10^1$ | $3 \times 10^6$ | $3 \times 10^4$ | $3 \times 10^1$ | $3 \times 10^2$ | $3 \times 10^1$ | $3 \times 10^1$ | $2 \times 10^3$ | 0 | 0 | 0 | 0 | 0 | 0 | 0 | 0 |
| *Escherichia coli* | 0 | $5 \times 10^1$ | $4 \times 10^2$ | $4 \times 10^4$ | $4 \times 10^1$ | $3 \times 10^9$ | $4 \times 10^1$ | $3 \times 10^3$ | $3 \times 10^2$ | $2 \times 10^6$ | $2 \times 10^1$ | 0 | 0 | 0 | 0 | 0 | 0 | 0 | 0 |
| *Pseudomonas aeruginosa* | 0 | $5 \times 10^2$ | $4 \times 10^3$ | $4 \times 10^9$ | $5 \times 10^2$ | $4 \times 10^7$ | $4 \times 10^9$ | $5 \times 10^1$ | $4 \times 10^7$ | $3 \times 10^2$ | $2 \times 10^3$ | $1 \times 10^2$ | 0 | $1 \times 10^4$ | 0 | 0 | 0 | 0 | 0 |

Here, arrows shown in Table 3 indicate operation times of respective devices. As can be understood from the result shown in Table 3, the propagation control of bacteria by the supply of oxygen and the radiation of ultrasonic waves is not observed. By circulating water under an oxygen rich state at a water temperature of 28° C., the bacteria served for the test are bred and activated. Even after the radiation of light from the blacklight is started, the propagation of the bacteria cannot be controlled immediately and the number of viable bacteria of the bacteria is once increased. However, it is found with reproducibility that that the bacteria except for *Pseudomonas aeruginosa* are subject to cell damage due to the oxidizing action of the active oxygen species contained in the photocatalytic reaction water and are sterilized. In addition, with respect to the *Pseudomonas aeruginosa*, it is found that the propagation of the bacteria can be controlled with the use of only the photocatalytic reaction. That is, the number of viable *Pseudomonas aeruginosa* is decreased immediately after the use of the sterilizing lamp together with the photocatalytic reaction water is started thus eliminating and sterilizing the bacteria.

That is, with respect to the *Pseudomonas aeruginosa* to which the bacteria elimination and sterilization effect is found to be small in the experiment 3, by using the sterilization lamp together with the photocatalytic reaction water, it is possible to acquire the bacteria elimination and sterilization effect rather than bacteria control effects. Further, it is also found that bacteria such as Gram-negative *bacillus* other than the bacteria served for the test are neither mixed into nor propagated in the water reservoir and hence, the water reservoir does not offer a propagation field for new bacteria. Accordingly, it is determined that there exists a synergistic effect between photocatalytic reaction water and the sterilizing lamp.

[Embodiment 4]

Next, an example which adopts the apparatus for producing photocatalytic reaction water according to the present invention as an apparatus for producing photocatalytic reaction water for eliminating parasites or protozoa is explained. The apparatus for producing photocatalytic reaction water according to the present invention exhibits the excellent parasites or protozoa elimination ability with respect to the parasites adhering to fish or the like. Hereinafter, an example of the constitution of the apparatus for producing photocatalytic reaction water for eliminating parasites or protozoa and a result of verification of the parasites or protozoa elimination effect acquired by using the apparatus are described.

[Example of Constitution of Apparatus for Producing Photocatalytic Reaction Water for Eliminating Parasites or Protozoa]

The apparatus for producing photocatalytic reaction water for eliminating parasites or protozoa and a method for eliminating parasites or protozoa using the apparatus are explained in conjunction with FIGS. 8 to 14 which show states in which the apparatus is used.

Figure 8:
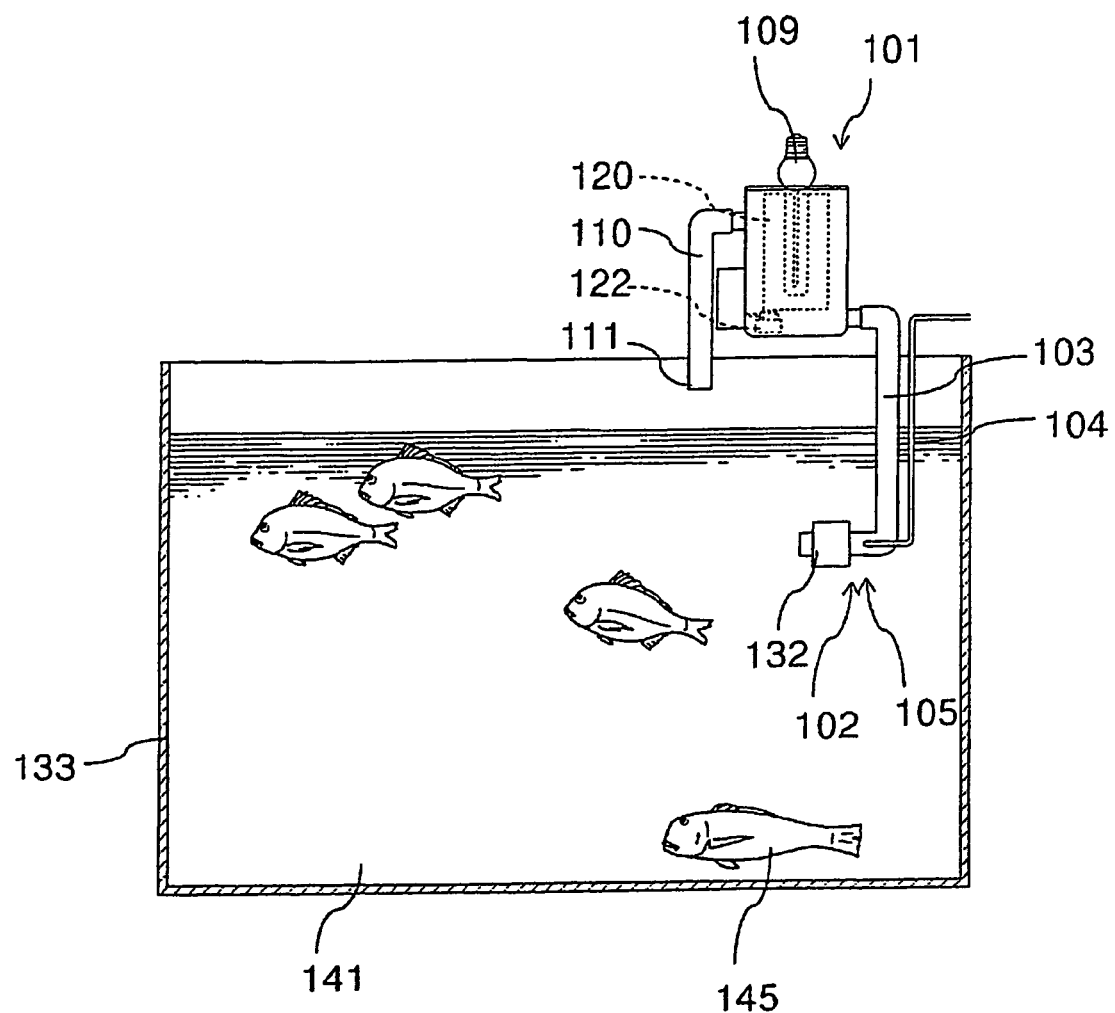
FIG. 8 is an explanatory view of the apparatus for producing photocatalytic reaction water for eliminating parasites according to the embodiment of the present invention.

FIG. 8 shows a state in which the apparatus 101 for producing photocatalytic reaction water for eliminating parasites or protozoa is arranged in the water reservoir 133, and sea water 142 stored in the water reservoir 133 is circulated through the apparatus 101 for producing photocatalytic reaction water for eliminating parasites or protozoa to allow sea water to contain active oxygen species.

Here, a water supply pump 132 is mounted on a distal end portion of a water supply port 102. By operating the water supply pump 132, sea water in which oxygen is dissolved can be supplied to an apparatus 101 for producing photocatalytic reaction water for eliminating parasites or protozoa through a water supply pipe 103.

Further, in sea water supplied to the apparatus 101 for producing photocatalytic reaction water for eliminating parasites or protozoa, a photocatalytic body 120 is excited by ultra violet rays radiated from an ultra violet ray lamp 109 and, at the same time, ultrasonic waves are generated from an ultrasonic vibrator 122. Accordingly, a large quantity of the active oxygen species is separated from the photocatalytic body and is effectively dissolved in sea water.

Sea water which contains the large quantity of active oxygen species passes through a water discharge pipe 110, is discharged from a discharge port 111, and flows into the water reservoir 133 again.

Fish 145 are held in the water reservoir 133 in advance and hence, water which contains the active oxygen discharged from the apparatus 101 for producing photocatalytic reaction water for eliminating parasites or protozoa affects microorganisms, parasites or the like which are adhered to fish 145 and can eliminate the parasites from fish 145. Here, the term "fish 145" implies not only adult fish but also larval fish.

Here, in FIG. 8, one apparatus 101 for producing photocatalytic reaction water for eliminating parasites or protozoa is mounted on one water reservoir 133. However, as shown in FIG. 9, the mounting number of apparatuses 101 for producing photocatalytic reaction water for eliminating parasites or protozoa may be increased corresponding to the number of fish 145 from which the parasites are to be eliminated, a quantity of sea water stored in the water reservoir 133 or desired active oxygen concentration of sea water.

Figure 9:
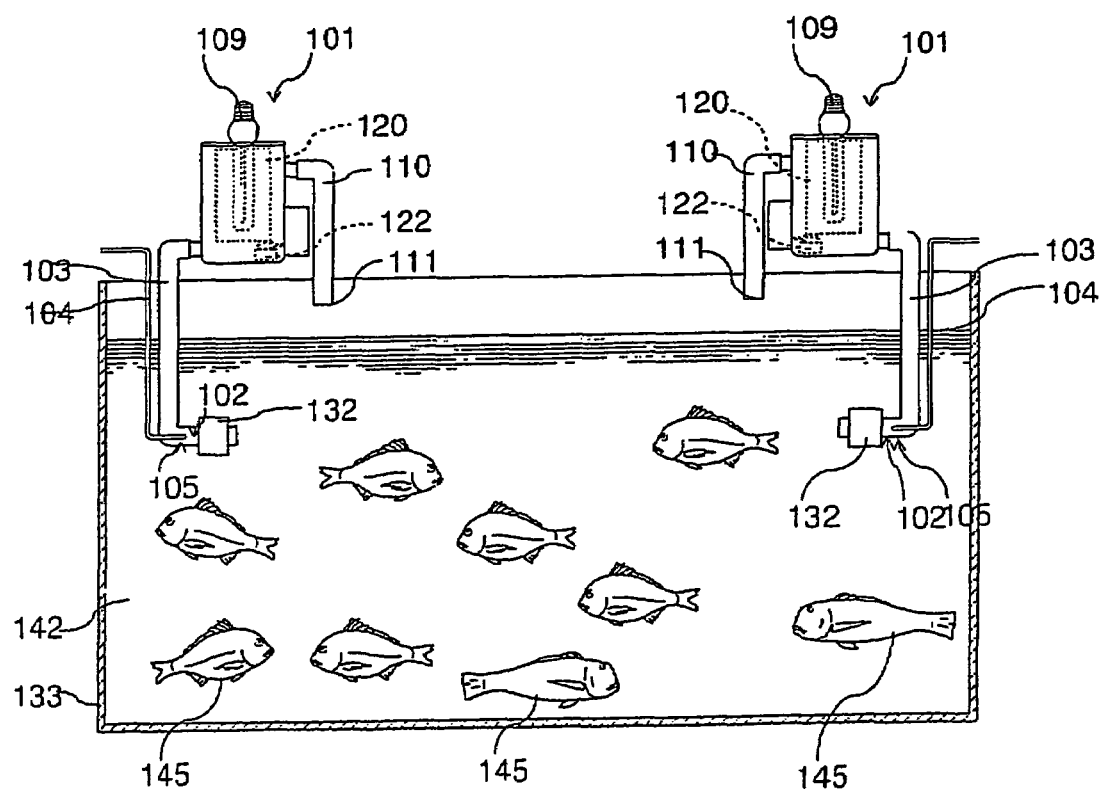
FIG. 9 is an explanatory view of the apparatus for producing photocatalytic reaction water for eliminating parasites according to the embodiment of the present invention.
Figure 10:
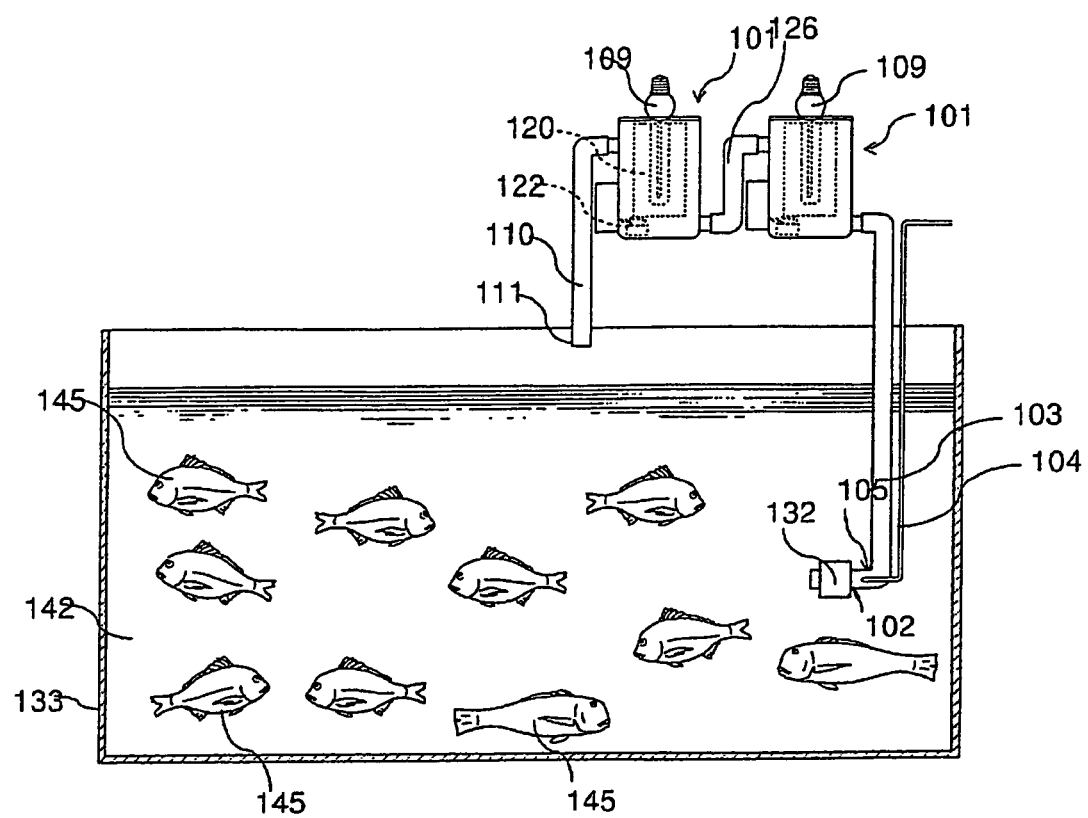
FIG. 10 is an explanatory view of the apparatus for producing photocatalytic reaction water for eliminating parasites according to the embodiment of the present invention.

Further, in FIG. 9, the apparatuses 101 for producing photocatalytic reaction water for eliminating parasites or protozoa are mounted on the water reservoir 133 in a parallel state. However, as shown in FIG. 10, the apparatuses 101 for producing photocatalytic reaction water for eliminating parasites or protozoa may be mounted on the water reservoir 133 in a serial state using a connection pipe 126. In this case, water discharged from the water discharge port 111 through two apparatuses 101 for producing photocatalytic reaction water for eliminating parasites or protozoa contains a larger quantity of the active oxygen compared to water discharged from one apparatus 101 for producing photocatalytic reaction water for eliminating parasites or protozoa. Accordingly, when water which contains active oxygen at high concentration is desired, two apparatuses 101 for producing photocatalytic reaction water for eliminating parasites or protozoa are preferably used.

[Use-State Example 2 of Apparatus for Producing Photocatalytic Reaction Water for Eliminating Parasites or Protozoa]

Next, an apparatus for producing photocatalytic reaction water for eliminating parasites or protozoa making use of photocatalytic reaction which also includes a sterilizer is explained while showing a use state of the apparatus.

Figure 11:
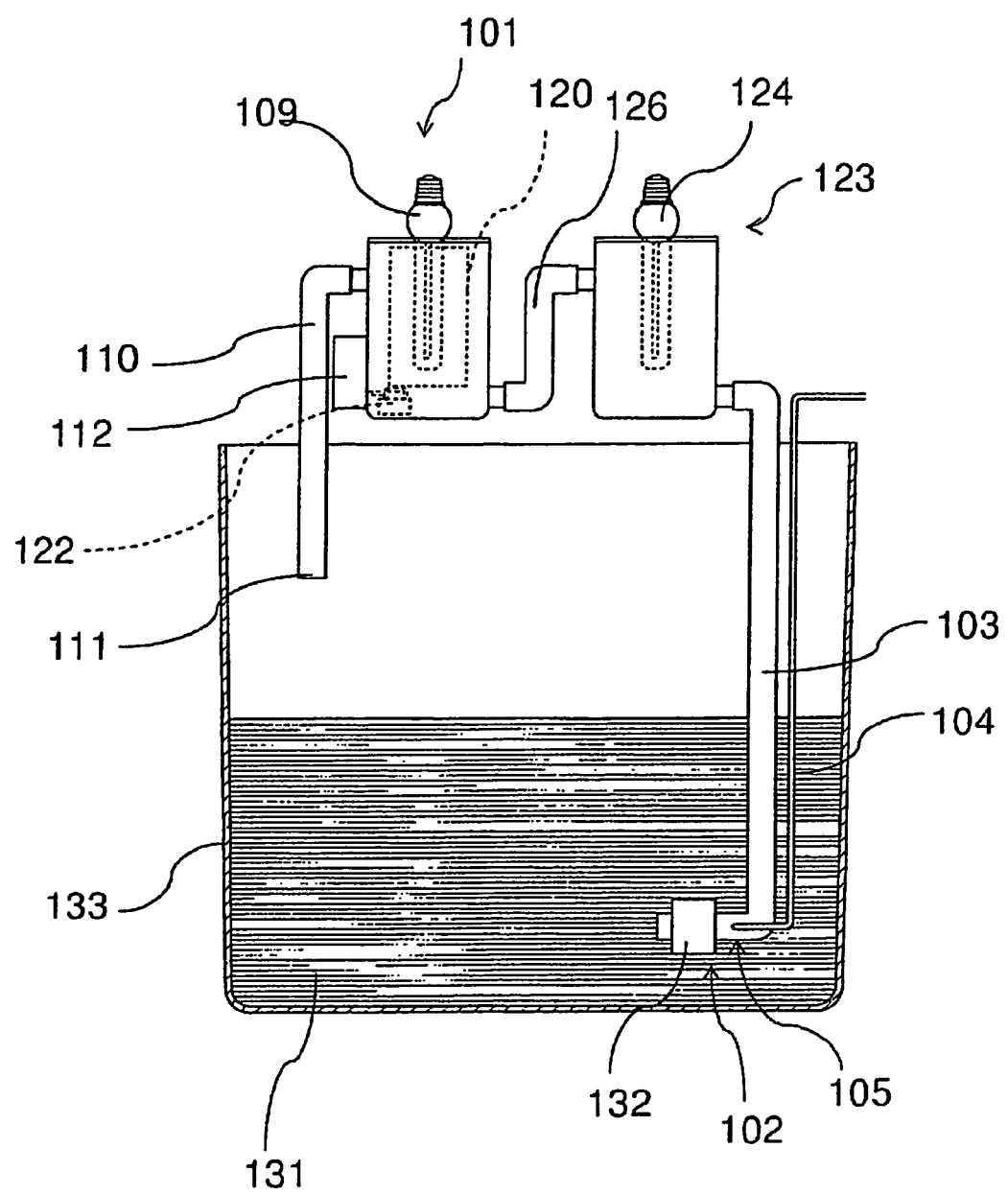
FIG. 11 is an explanatory view of the apparatus for producing photocatalytic reaction water for eliminating parasites according to the embodiment of the present invention.

That is, as shown in FIG. 11, between a water supply pump 132 which is immersed in water 131 stored in the water reservoir 133 and the apparatus 101 for producing photocatalytic reaction water for eliminating parasites or protozoa, a sterilizer 123 including a sterilizing lamp 124 is arranged. Ultra violet rays radiated from the sterilizing lamp 124 can be radiated to water 131 which circulates in the inside of the sterilizer 123.

A sterilizing lamp 124 mounted on the sterilizer 123 can radiate ultra violet rays having a wavelength of 245 to 265 nm, and more preferably, a wavelength of 256 nm, and as described in the explanation of apparatus for producing photocatalytic reaction water for eliminating bacteria, the sterilizing lamp 124 can sterilize the microorganisms by giving damages attributed to the mutation disorder to DNA of the microorganisms in water.

Further, the sterilizer and a pipe for supplying water which already passed through the sterilizer to the apparatus 101 for producing photocatalytic reaction water for eliminating parasites or protozoa re shielded from external visible light.

A mirror surface formed on a wall surface of the apparatus 101 for producing photocatalytic reaction water for eliminating parasites or protozoa also possesses an effect to prevent the recovery of bacteria by receiving light. By preventing the recovery of bacteria by receiving light, it is possible to efficiently give the damages attributed to the ultra violet rays having wavelength of 245 to 265 nm to the microorganisms thus enhancing the sterilization effect.

Further, sterilized bacterial cells or weakened microorganisms are supplied to the apparatus 101 for producing photocatalytic reaction water for eliminating parasites or protozoa and are brought into contact with the activate oxygen species generated in the photocatalytic body or the like and hence, it is possible to surely sterilize the microorganisms in water by decomposing the bacteria cells with oxidation or by giving fatal damage to the weakened microorganims.

Water 131 treated in the sterilizer 123 in such a mechanism is supplied to the apparatus 101 for producing photocatalytic reaction water for eliminating parasites or protozoa through the connection pipe 126 which connects the sterilizer 123 and the apparatus 101 for producing photocatalytic reaction water for eliminating parasites or protozoa.

In this apparatus 101 for producing photocatalytic reaction water for eliminating parasites or protozoa, the active oxygen species and the like are diffused in water and hence, the microorganisms which arrive at the apparatus 101 for producing photocatalytic reaction water for eliminating parasites or protozoa without being sterilized by the sterilizer but weakened by the damage of cell membranes are completely sterilized receiving fatal damage attributed to the application of active oxygen species.

[Use-State Example 3 of Apparatus for Producing Photocatalytic Reaction Water for Eliminating Parasites or Protozoa]

Figure 12:
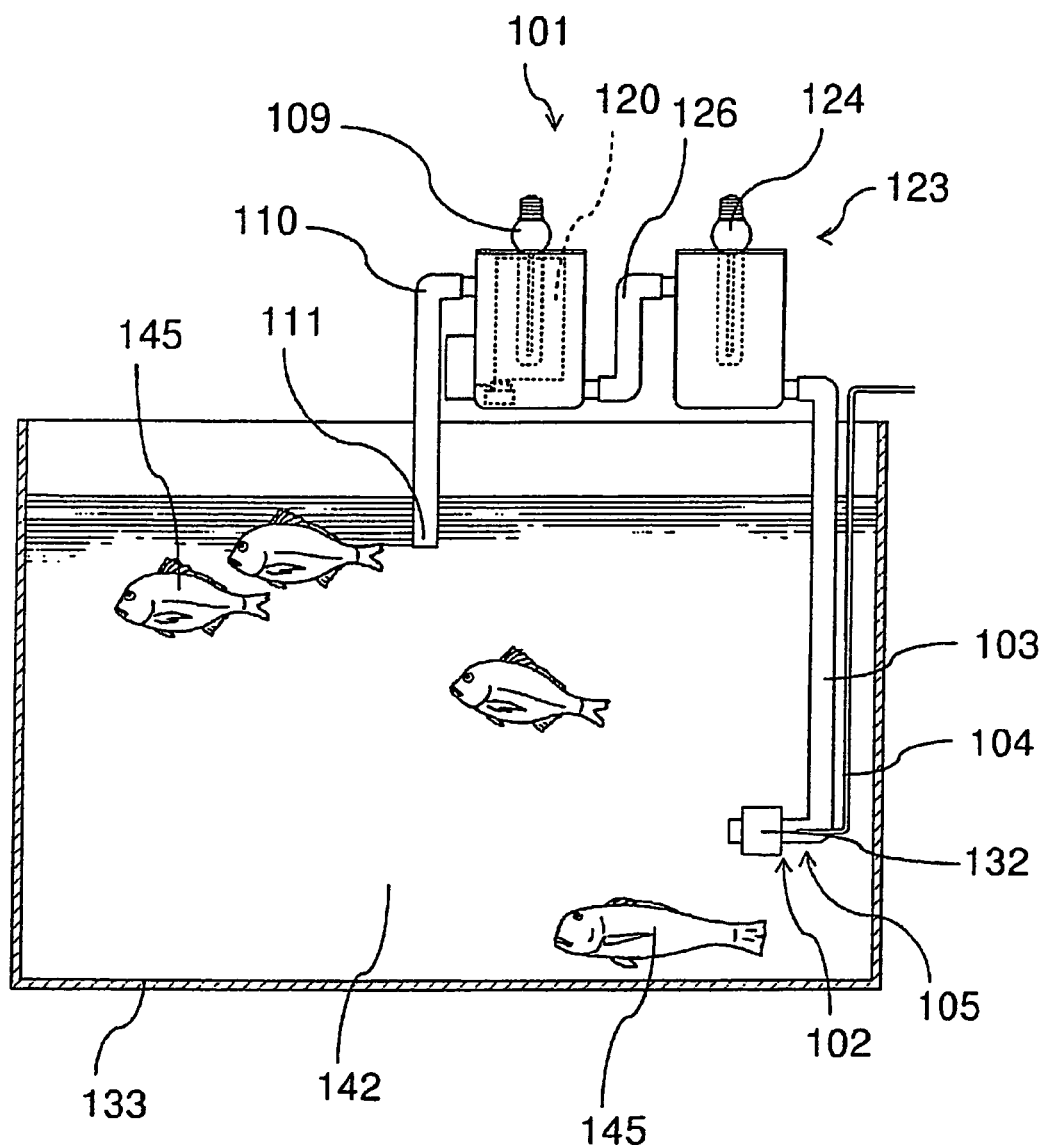
FIG. 12 is an explanatory view of the apparatus for producing photocatalytic reaction water for eliminating parasites according to the embodiment of the present invention.

Next, an example in which the parasites or microorganisms adhering to the fish are eliminated by bringing fish into contact with water which contains the active oxygen species generated through the apparatus 101 for producing photocatalytic reaction water for eliminating parasites or protozoa and the sterilizer 123 is explained in conjunction with FIG. 12.

10 liters of sea water 142 are stored in the water reservoir 133, and the apparatus 101 for producing photocatalytic reaction water for eliminating parasites or protozoa which includes the sterilizer 123 is mounted on an upper portion of the water reservoir 133.

By preliminarily operating the apparatus 101 for producing photocatalytic reaction water for eliminating parasites or protozoa for 1 hour, sea water temperature is adjusted to 28° C., and the dissolved oxygen concentration (DO) is adjusted to 6.8 mg/L. The test is performed while maintaining sea water temperature and dissolved oxygen concentration at fixed values even after the adjustment of sea water temperature and the dissolved oxygen concentration. The concentration of hydrogen peroxide water in circulating photocatalytic reaction water is always held at 3 ppm or less.

Then, as shown in Table 4, fish 145 which are subject to the test are allowed to swim in the water reservoir.

TABLE 4

| kind of fish | length | weight | average number of Heteraxine heterocerca per fish |
|---|---|---|---|
| seriola | 14 cm | 40 g | 20 |
| seriola | 14 cm | 40 g | |
| seriola | 14 cm | 40 g | |
| seriola | 14 cm | 40 g | |
| tiger puffer | not measured | 40 g | 30 |
| tiger puffer | not measured | 40 g | |
| tiger puffer | not measured | 40 g | |
| tiger puffer | not measured | 40 g | |

As shown in Table 4, four seriolas and four tiger puffers are held in the water reservoir. Here, gills of these fish 145 are preliminarily examined. As a result of the examination, the number of *Heteraxine heterocerca* adhering to each seriola is 20 in average, and the number of *Heteraxine heterocerca* adhering to each tiger puffer is 30 in average.

Then, after operating the apparatus 101 for producing photocatalytic reaction water for eliminating parasites or protozoa in the water reservoir for circulating water for two hours, the apparatus 101 is stopped. Then, two seriolas and two tiger puffers are taken out, and a state of *Heteraxine heterocerca* adhering to fish 145 is observed. Remaining two seriolas and two tiger puffers are returned to a fish preserve in the sea and, after twenty hours, a state of *Heteraxine heterocerca* adhering to fish 145 is checked. The result is shown in Table 5.

TABLE 5

| | kind of fish | length | weight | number of survived Heteraxine heterocerca | average number of Heteraxine heterocerca per fish |
|---|---|---|---|---|---|
| Just after test | seriola | 14 cm | 40 g | 15 | 17 |
| | seriola | 14 cm | 40 g | 19 | |
| | tiger puffer | not measured | 40 g | 17 | 15 |
| | tiger puffer | not measured | 40 g | 13 | |
| 20 hours after test | seriola | 14 cm | 40 g | 0 | 0 |
| | seriola | 14 cm | 40 g | 0 | |
| | tiger puffer | not measured | 40 g | 2 | 2.5 |
| | tiger puffer | not measured | 40 g | 3 | |

As shown in Table 5, the apparatus 101 for producing photocatalytic reaction water for eliminating parasites or protozoa 101 is operated for two hours. With respect to fish 145 consisting of two seriolas and two tiger puffers, immediately after the operation of the apparatus 101 is finished, the number of *Heteraxine heterocerca* adhering to the seriola is 17 in average, and the number of *Heteraxine heterocerca* adhering to the tiger puffer is 15 in average. That is, the number of *Heteraxine heterocerca* adhering to fish 145 is substantially halved. Further, the activity of *Heteraxine heterocerca* is lowered.

With respect to remaining fish 45 consisting of two seriolas and two tiger puffers, after a lapse of twenty hours from the finishing of the operation of the apparatus 101, the number of

*Heteraxine heterocerca* adhering to the seriola is 0 in average, and the number of *Heteraxine heterocerca* adhering to the tiger puffer is 2.5 in average. That is, the number of *Heteraxine heterocerca* adhering to fish 45 is remarkably decreased.

From these results, it is considered that water containing active oxygen species which is produced by the apparatus 101 for producing photocatalytic reaction water for eliminating parasites or protozoa can eliminate *Heteraxine heterocerca* without using hydrogen peroxide water. The apparatus 101 for producing photocatalytic reaction water for eliminating parasites or protozoa, first of all, purifies sea water. Then, the purified water extremely effectively affects *Heteraxine heterocerca* adhering to fish 145 thus eliminating *Heteraxine heterocerca*.

[Use-State Example 4 of Apparatus for Producing Photocatalytic Reaction Water for Eliminating Parasites or Protozoa]

Next, in conjunction with FIG. 12, the explanation is made with respect to an example in which parasites or microorganisms adhering to fish are eliminated by bringing water containing active oxygen species produced by the apparatus 101 for producing photocatalytic reaction water for eliminating parasites or protozoa and the sterilizer 123 into contact with fish.

30 liters of sea water 142 are filled in the water reservoir 133, and an apparatus 101 for producing photocatalytic reaction water for eliminating parasites or protozoa which includes a sterilizer 123 is arranged at an upper portion of a water reservoir 133.

Two sets of water reservoirs 133 each of which is provided with the apparatus 101 for producing photocatalytic reaction water for eliminating parasites or protozoa are prepared. By operating the apparatus 101 for producing photocatalytic reaction water for eliminating parasites or protozoa of each water reservoir 133 for 1 hour, sea water temperature is adjusted to 28° C., and dissolved oxygen concentration (DO) is adjusted to 6.8 mg/L. The test is performed while maintaining sea water temperature and dissolved oxygen concentration at fixed values. Further, in the same manner as the embodiment 5, the concentration of hydrogen peroxide water of circulating photocatalytic reaction water is always set to 3 ppm or less.

Further, as shown in Table 6, fish 145 which are subject to the test are allowed to swim in the respective water reservoirs. Here, the explanation is made by naming one set of water reservoir 133 out of two sets of water reservoirs 133 as the water reservoir A, and another water reservoir 133 out of two sets of water reservoirs 133 as the water reservoir B.

TABLE 6

| water reservoir | kind of fish | length | weight | an average number of Heteraxine heterocerca per fish |
|---|---|---|---|---|
| water reservoir A | seriola | 14.0 cm | 40 g | 20 |
| | seriola | 14.0 cm | 40 g | |
| | seriola | 21.5 cm | 110 g | |
| | seriola | 21.5 cm | 110 g | |
| | seriola | 21.5 cm | 110 g | |
| | seriola | 21.5 cm | 110 g | |
| | tiger puffer | not measured | 40 g | |
| water reservoir B | seriola | 14.0 cm | 40 g | 20 |
| | seriola | 21.5 cm | 110 g | |
| | seriola | 21.5 cm | 110 g | |
| | seriola | 21.5 cm | 110 g | |
| | seriola | 21.5 cm | 110 g | |

As shown in Table 6, six seriolas and one tiger puffer are held in the water reservoir A, while five seriolas are held in the water reservoir B. Here, gills of these fish 145 are preliminarily examined. As a result of the examination, the number of *Heteraxine heterocerca* adhering to fish is 20 per fish in average in both water reservoirs.

Then, the test is started by operating the apparatus 101 for producing photocatalytic reaction water for eliminating parasites or protozoa in both water reservoirs. Here, the apparatus 101 for producing photocatalytic reaction water for eliminating parasites or protozoa in the water reservoir A is operated for four hours, and apparatus 101 for producing photocatalytic reaction water for eliminating parasites or protozoa in the water reservoir B is operated for six hours and, thereafter, both apparatuses 101 are stopped. After twenty hours, a state of *Heteraxine heterocerca* adhering to fish 145 is checked. The result is shown in Table 7.

TABLE 7

| water reservoir | kind of fish | length | weight | a number of survived Heteraxine heterocerca | an average number of Heteraxine heterocerca per a fish |
|---|---|---|---|---|---|
| water reservoir A | seriola | 14.0 cm | 40 g | 4 | 3 |
| | seriola | 14.0 cm | 40 g | 4 | |
| | seriola | 21.5 cm | 110 g | 5 | |
| | seriola | 21.5 cm | 110 g | 4 | |
| | seriola | 21.5 cm | 110 g | 4 | |
| | seriola | 21.5 cm | 110 g | 1 | |
| | tiger puffer | not measured | 40 g | 2 | |
| water reservoir B | seriola | 14.0 cm | 40 g | 1 | 1 |
| | seriola | 21.5 cm | 110 g | 0 | |
| | seriola | 21.5 cm | 110 g | 4 | |
| | seriola | 21.5 cm | 110 g | 0 | |
| | seriola | 21.5 cm | 110 g | 0 | |

As shown in Table 7, when the apparatus 101 for producing photocatalytic reaction water for eliminating parasites or protozoa 101 is operated for 4 hours and, thereafter, twenty hours elapses from stopping of the operation of the apparatus 101, the number of *Heteraxine heterocerca* adhering to fish 145 in the water reservoir A is 3 in average.

Further, when the apparatus 101 for producing photocatalytic reaction water for eliminating parasites or protozoa 101 is operated for 6 hours and, thereafter, twenty hours elapses from stopping of the operation of the apparatus 101, the number of *Heteraxine heterocerca* adhering to fish 145 in the water reservoir B is 1 in average.

It is understood from these results that water containing active oxygen species which is produced by the apparatus 101 for producing photocatalytic reaction water for eliminating parasites or protozoa extremely effectively acts on *Heteraxine heterocerca* adhering to fish 145 thus eliminating *Heteraxine heterocerca*.

Further, what must be particularly pointed out in the result is that in spite of a fact that fish 145 is weakened attributed to adhesion of *Heteraxine heterocerca* to fish 145, the number of dead fish is zero. This implies that water containing active oxygen species which is produced by the apparatus 101 for producing photocatalytic reaction water for eliminating parasites or protozoa has the strong parasite elimination effect against *Heteraxine heterocerca* while extremely gently acting on fish 145 thus hardly adversely influencing fish 145.

Further, the parasite elimination effect of water containing active oxygen species against the parasites is attributed to the active oxygen species or the like and hence, there is no possibility that parasites or the microorganisms acquire resistance thus allowing a user to use water containing active oxygen species for a long period.

Further, water containing active oxygen species which is used for eliminating the parasites or the microorganisms is speedily transformed into substances such as water, oxygen or the like even water is discharged in nature and hence, there is no possibility of adversely influencing the environment.

In addition to the above, water containing active oxygen species adhering to fish, the parasites, the microorganisms or the like is speedily transformed into substances such as water, oxygen or the like and hence, medicament does not remain in the fish whereby there is no possibility that a consumer image is lowered.

In this manner, processing may be performed by bringing water containing active oxygen species into contact with water in which fish 145 live. However, the substantially same advantageous effect can be acquired by immersing fish 145 into water containing active oxygen species which is preliminarily stored in a water reservoir for a predetermined time.

Further, to alleviate the invasion of strong activation oxygen, controlled release carbonate calcium, baked new century tubercle coral or the like may be mixed into the water circulation circuit.

In addition to the above, to prevent the lowering of generation efficiency of the activation oxygen attributed to the adhesion of contaminant floating in water, parasites such as *Heteraxine heterocerca* falling from the fish body or the like to the photocatalytic body 120, a filter may be arranged in a flow passage of water supplied to the apparatus 101 for producing photocatalytic reaction water for eliminating parasites or protozoa from a water supply pump 132.

In this embodiment, the explanation has been made with respect to a casein which fish 145 are cultivated fish. However, it is needless to say that the present invention is applicable to a case in which fish 145 are admiration fish. Particularly, when the apparatus 101 for producing photocatalytic reaction water for eliminating parasites or protozoa is applied to a water reservoir in which admiration fish are bred at an ordinary household, to periodically supply water containing active oxygen species into the water reservoir 133 or to prevent the supply of water containing an excessive quantity of active oxygen species into water stored in the water reservoir 133, a timer or a limiter which controls the supply of electricity to an ultra violet ray lamp 109 may be provided. Due to such a constitution, it is possible to keep favorable health condition of the admiration fish all the time.

Further, when the supply of electricity to the ultra violet ray lamp 109 is stopped, water containing a sufficient quantity of oxygen is supplied to water stored in the water reservoir 133 from the discharge port 111 and hence, it is possible to maintain favorable propagation environment for fish 145.

[Use-State Example 4 of Apparatus for Producing Photocatalytic Reaction Water for Eliminating Parasites or Protozoa]

As has been explained heretofore, by arranging the apparatus for producing photocatalytic reaction water for eliminating parasites or protozoa in a water reservoir or the like, it is possible to eliminate parasites adhering to fish held in a water reservoir. However, in the embodiment 6, the explanation is made with respect to an example in which whole water reservoir constitutes the apparatus for producing photocatalytic reaction water for eliminating parasites or protozoa.

Figure 13:
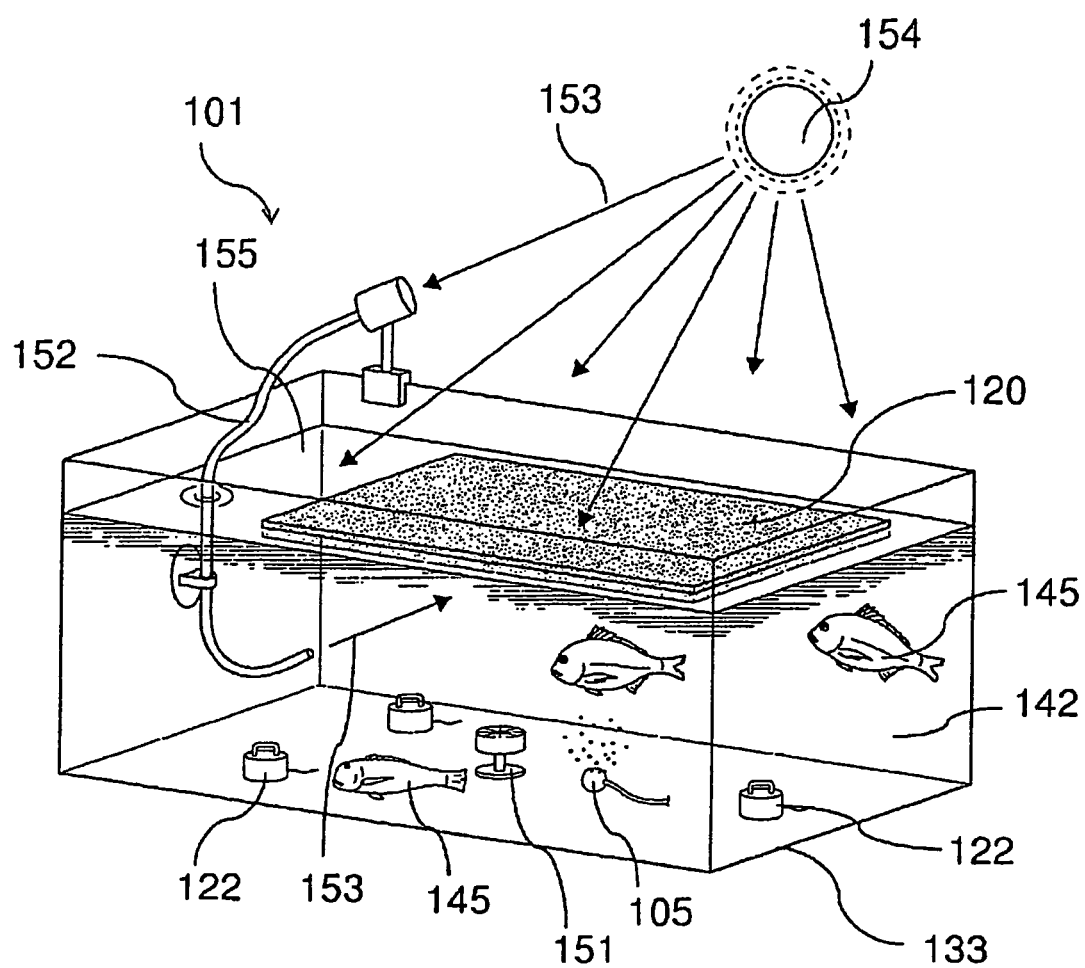
FIG. 13 is an explanatory view of the apparatus for producing photocatalytic reaction water for eliminating parasites according to the embodiment of the present invention.

That is, in the apparatus 101 for producing photocatalytic reaction water for eliminating parasites or protozoa shown in FIG. 13, on a bottom portion of the water reservoir 133 in which fish 145 to which parasites adhere and sea water 142 are stored, an ultrasonic wave oscillator 122 connected to an ultrasonic wave generator not shown in the drawing, a water fan 151 and an oxygen supply portion 105 are arranged.

Further, a photocatalytic body 120 formed in a sheet-like shape is arranged on a water surface 155, wherein sun light 153 radiated from the sun 154 impinges on an upper surface of the photocatalytic body 120 thus exciting the photocatalytic body 120.

Here, the photocatalytic body 120 may float on the water surface 155 by forming the carrier using a material capable of floating on water, or by attaching a float to the photocatalyst.

Here, by arranging a reflector 152 at a predetermined position in the water reservoir 133 and in sea water 142, the sun light 153 is guided to the inside of sea water 142 and hence, it is possible to radiate the sun light from a back surface of the photocatalytic body 120.

The reflector 152 is not particularly limited provided that the reflector 152 can guide light into the inside of sea water 142 and enables the radiation of light to the photocatalytic body 120 from the back surface thereof. For example, the reflector 152 may be made of optical fibers or an optical prism.

Due to such a constitution, in the apparatus 101 for producing photocatalytic reaction water for eliminating parasites or protozoa, by guiding the sun light 153 by the reflector 152 and by radiating the light to the back surface of the photocatalytic body 120, the photocatalytic body 120 is excited.

The excited photocatalytic body 120 generates the active oxygen species, and the active oxygen species are diffused in sea water 142 by the ultrasonic waves generated by the ultrasonic wave oscillator 122 and by the water fan 151 mounted on the bottom portion of the water reservoir 133.

The diffused active oxygen species act on the parasites adhering to fish 145 using sea water 142 as a medium thus exhibiting a parasites and protozoa elimination effect.

Here, when the apparatus 101 for producing photocatalytic reaction water for eliminating parasites or protozoa having such a constitution is continuously used, there may be a case in which organisms or stains are adhered to the back surface of the photocatalytic body 120 (the surface to which light is radiated by the reflector 152). Particularly, spores of the seaweed and larva of the shellfish are floating in sea water 142 and hence, when these are implanted on the photocatalytic body 120 and grow, the area of the photocatalytic body 120 which can receive light is decreased and hence, the generation of the active oxygen species by the photocatalytic body 120 is prevented.

Accordingly, the sheet-like photocatalytic body 120 shown in FIG. 13 is configured to be reversible so that the surface to which seaweed and shellfish do not adhere can be immersed in water and hence, it is possible to efficiently generate the active oxygen species.

Further, the surface to which the seaweed or the shellfish adhere is exposed to and dried by the sun beams and hence, the seaweed or the shellfish die out and, further, these deposits are removed due to a stain preventing effect which is one of typical effects of the photocatalyst.

The surface of the photocatalytic body 120 from which the deposits are removed is again immersed in sea water 142 by reversing the inside and outside of the photocatalytic body 120 thus efficiently generating the active oxygen species.

Figure 14:
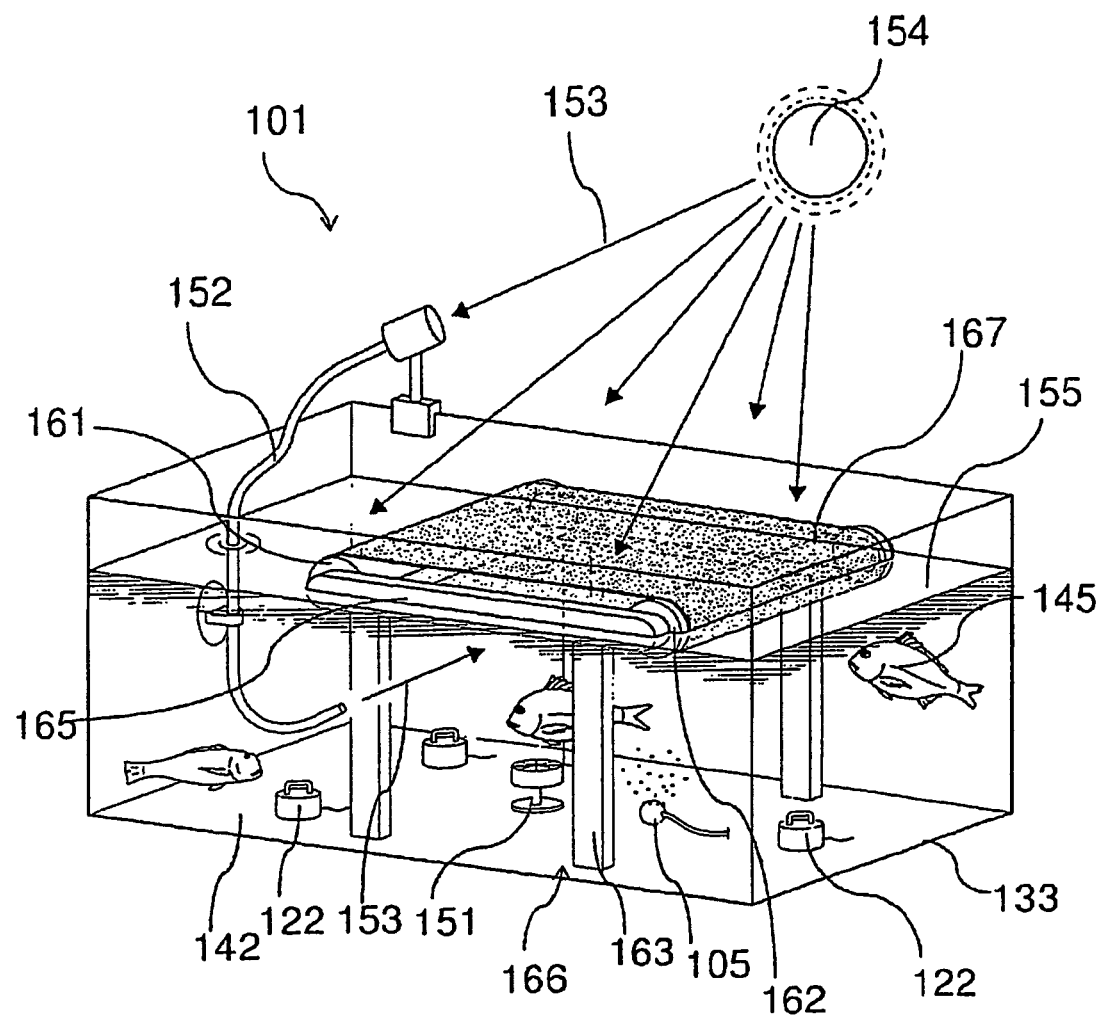
FIG. 14 is an explanatory view of the apparatus for producing photocatalytic reaction water for eliminating parasites according to the embodiment of the present invention.

Further, an example which further facilitates the inside-and-outside reversing operation is shown in FIG. 14.

FIG. 14 shows an apparatus 101 for producing photocatalytic reaction water for eliminating parasites or protozoa having the substantially same constitution as the apparatus 101 for producing photocatalytic reaction water for eliminating parasites or protozoa shown in FIG. 13 except for that the apparatus 101 shown in FIG. 14 differs from the apparatus 101 shown in FIG. 14 with respect to the constitution of the photocatalytic body 120.

That is, in the apparatus 101 for producing photocatalytic reaction water for eliminating parasites or protozoa shown in FIG. 14, a parallel rods 165 extend between two supports 163, 163 mounted upright on the bottom surface of the water reservoir 133 to form a support portion 166, and two sets of support portions 166 are arranged in the water reservoir 133. Here, a drive roller 161 is interposed between one ends of the parallel rods 165 which are arranged parallel to each other at a predetermined distance there between, and a driven roller 162 is interposed between another ends of the parallel rods 165. Further, the photocatalyst sheet body 167 formed in an endless loop shape extends between and is wound around the drive roller 161 and the driven roller 162, and the photocatalyst sheet body 167 is rotatably driven.

Further, the parallel rods 165 are arranged on the water surface 155 of sea water 142 in a state that approximately half of the photocatalyst sheet body 167 is immersed in sea water 142 and remaining approximately half of the photocatalyst sheet body 167 is exposed above the water surface 155.

Accordingly, by operating the drive roller 161, the photocatalyst sheet body 167 is flexibly driven and hence, it is possible to easily expose the surface to which the seaweed or the shellfish adhere above the water surface 155, while the surface from which the deposits are removed above the water surface 155 is pulled down to a position below the water surface 155, and immersed in sea water 142.

Accordingly, the active oxygen species are efficiently generated by from the photocatalyst sheet body 167 and hence, it is possible to eliminate parasites adhering to fish 154.

Here, in FIG. 13 and FIG. 14, the apparatus 101 for producing photocatalytic reaction water for eliminating parasites or protozoa is constituted using the water reservoir 133. However, the apparatus 101 is not limited to such a constitution. For example, in place of the water reservoir 133, using a fish preserve formed of a fish net arranged in sea water in an extending manner, it is possible to eliminate parasites or protozoa adhering to a large quantity of fish while performing cultivation of fish.

In this case, by imparting a function of photocatalyst to the fish net for forming the fish preserve, it is possible to form the photocatalytic body 120.

Particularly, in many cases, parasites adhering to fish infect other fish by way of the fish net of the fish preserve and hence, by imparting a photocatalytic function to the fishing net so as to form the photocatalytic body 120 and by radiating light to the photocatalytic body 120, it is possible to easily cut off an infection route of the parasites.

Further, in FIG. 13 and FIG. 14, light radiated from the sun 154 is used as light for exciting the photocatalytic body 120 or the photocatalyst sheet body 167. However, it is needless to say that, as described in conjunction with the above-mentioned embodiments, a light source which radiates light for exciting the photocatalytic body 120 or the photocatalyst sheet body 167 may be a light source which can radiate ultra violet rays having at least a wavelength of 350 to 370 nm such as a blacklight, for example.

As described above, according to the apparatus for producing photocatalytic reaction water according to the present invention, it is possible to efficiently eliminate fish parasites bodies while saving electricity in a compact shape without using additional medicament or the like and without damaging an environment.

The apparatus for producing photocatalytic reaction water according to the present invention described in the embodiment 3, exhibits the excellent elimination and sterilization ability against the microorganisms. Further, in the apparatus for producing photocatalytic reaction water for eliminating parasites or protozoa described in the embodiment 4, it is confirmed that the efficacy of the photocatalytic reaction water is acquired not only in a place where the reaction occurs but also in a place remote from the place where the reaction occurs. Further, the efficacy of the photocatalytic reaction water is acquired not only during the reaction time but also after some time elapses. Hereinafter, some cases in which the apparatus for producing photocatalytic reaction water of the present invention which exhibits the above-mentioned excellent bacteria elimination ability, the bacterial sterilizing ability and the parasite or protozoa elimination ability is applied to daily commodities or the like are explained.

(i) Example in which Apparatus for Producing Photocatalytic Reaction Water of the Present Invention is Used in Sterilizer Installed in Circulating Water Passage.

First of all, there is described an example in which the apparatus for producing photocatalytic reaction water of the present invention is used in the treatment of microorganisms in hot water circulated in a bathtub or in circulation water in an outdoor machine of a cooling unit. By arranging the apparatus 1 for producing photocatalytic reaction water in a circulation water treatment circuit, it is possible to sterilize *Legionella* fungus which causes a serious problem recently.

That is, *Legionella* fungus lives in an environment such as water or wet soil and is a gram negative *bacillus* which likes a living environment at an optimum temperature of 15 to 43° C. A large number of *Legionella* fungus grows in the inside of cells of protozoa (amoeba) living in water a bathtub in which hot water is circulated, an air conditioner, or an outdoor machine attached to a cooling unit such as a freezer or a refrigerator.

Further, it is known that a large number of *Legionella* fungus grows in the inside of cells of protozoa (amoeba) and human being is infected with *Legionella* fungus when they directly inhale moisture containing a large quantity of fungus bodies discharged from the protozoa. That is, a same a sure to sterilize *Legionella* fungus, a process which realizes both of the sterilization of *Legionella* fungus per se and the sterilization of *Legionella* fungus which breaks cell membranes of protozoa and attempts to propagate in the cell membranes becomes important. The mere ability of sterilizing *Legionella* fungus per se is not sufficient.

Here, in addition to the usual sterilization, the elimination of protozoa to which bacteria adhere becomes necessary and hence, the stronger oxidizing ability becomes necessary.

However, with the use of the photocatalytic reaction water generated by the apparatus 1 for producing photocatalytic reaction water described in this embodiment, as explained in conjunction with the embodiment 4, it is possible to eliminate the parasites which adhere to fish and, at the same time, it is possible to eliminate the protozoa weaker than the parasites.

That is, since the protozoa can be sterilized and, at the same time, *Legionella* fungus which lives in the protozoa can be also sterilized, it is possible to prevent the infectious disease caused by *Legionella* fungus.

Here, for acquiring a sterilizing effect in many application fields and for maintaining a strong sterilizing ability, the use of a sterilizing lamp along with the apparatus for producing photocatalytic reaction water of the present invention is recommended.

(ii) Example in which Apparatus for Producing Photocatalytic Reaction Water of the Present Invention is Used for Treatment of Ballast Water in Ship Next, there is described an example in which the apparatus for producing photocatalytic reaction water of the present invention is used in the treatment of harmful organic substance and microorganisms contained in ballast water for adjusting the center of gravity and buoyancy of a ship. For example, by arranging the apparatus for producing photocatalytic reaction water of the present invention in the inside of ballast tank of the ship, or in a water discharge port for discharging ballast water, it is possible to treat ballast water safely and effectively without adding any other medicaments.

The ship adjusts the center of gravity and buoyancy thereof by introducing sea water into a ballast tank. In many cases, however, water (ballast water) which is introduced into the ballast tank is discharged at a place on sea different from the place where the water is taken.

For example, with respect to a large ship which sails on open sea with small shipment, the ship ensures stability thereof by increasing a weight thereof with the introduction of ballast water into the ballast tank. In loading the shipment after arriving at the destination in a foreign country, ballast water is discharged to make the ship light in weight thus adjusting the ship weight.

However, many microorganisms and organic substances live in sea water. Accordingly, there exists a possibility that when such ballast water is discharged in sea at a remote place, the ecosystem or an environment at a water discharge place is destroyed.

Particularly, marine organisms or the like which are carried to the water discharging place may grow abnormally by destroying food-chain in the water discharge place thus largely damaging cultivation industry.

Accordingly, by arranging the apparatus 1 for producing photocatalytic reaction water of the present invention in the ballast tank of the ship and by circulating ballast water in the apparatus 1 for producing photocatalytic reaction water, it is possible to sterilize the microorganisms which live in ballast water. Further, the apparatus 1 for producing photocatalytic reaction water can also decompose the harmful organic substances contained in ballast water.

Further, when the photocatalytic reaction water is produced by circulating ballast water in the apparatus 1 for producing photocatalytic reaction water, it is possible to prevent shellfish and seaweed from adhering to the inside of ballast tank.

Further, this embodiment describes the case in which the apparatus 1 for producing photocatalytic reaction water is arranged in the blast tank or the water discharge port of the ship as the means for treating the ballast water. However, it is not always necessary to arrange the apparatus 1 for producing photocatalytic reaction water in such a place. That is, the apparatus 1 for producing photocatalytic reaction water may be arranged in a port where the ship anchors where ballast water is collected by a pump, for example, and is discharged to sea after being treated by the apparatus 1 for producing photocatalytic reaction water.

In this manner, by treating ballast water in the apparatus 1 for producing photocatalytic reaction water, it is possible to prevent the destruction of the ecosystem and the environmental pollution attributed to the harmful organic substances. Further, compared to a case in which ballast water is treated using other chemicals, it is also possible to treat ballast water and, thereafter, to discharge ballast water to sea while suppressing the adverse influence on the environment.

Figure 15:
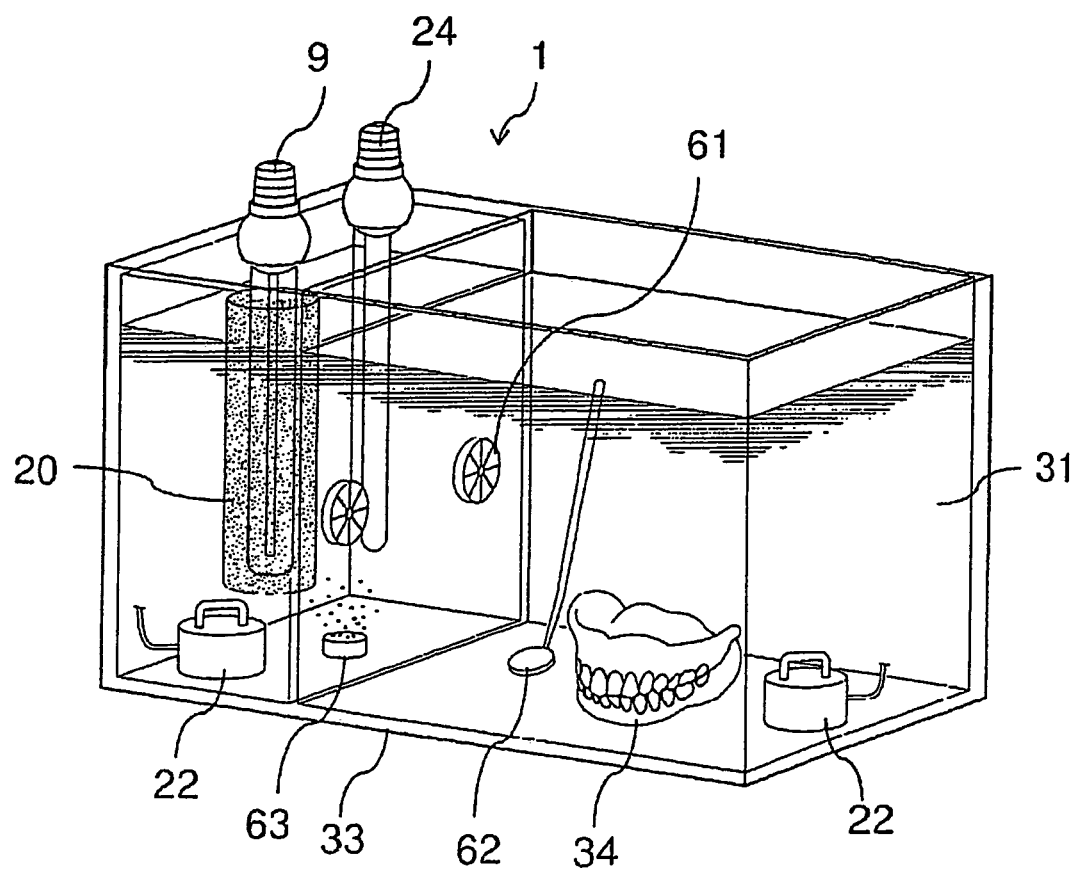
FIG. 15 is an explanatory view of the apparatus for producing photocatalytic reaction water according to the embodiment of the present invention.

(iii) Example in which Apparatus for Producing Photocatalytic Reaction Water of the Present Invention is Used for Cleaning Artificial Teeth Next, the explanation is made with respect to an example in which an artificial teeth 34 worn in oral cavity is sterilized using photocatalytic reaction water in conjunction with FIG. 15. By arranging the apparatus 1 for producing photocatalytic reaction water of the present invention in the water reservoir 33 having a predetermined volume and by immersing the artificial teeth 34 in photocatalytic reaction water stored in the water reservoir 33, it is possible to acquire an excellent cleaning effect, an excellent sterilization effect and an excellent elimination effect without adding any other medicaments.

That is, dregs of the food, tar of the tobacco and the like are liable to deposit on the artificial teeth 34 worn in oral cavity and hence, it is necessary to clean the artificial teeth 34 frequently. However, it is difficult to remove stains deposited on the artificial teeth 34 and hence, much effort such as vigorous teeth brushing for a long time is required.

Further, since the artificial teeth 34 is worn in oral cavity, it is impossible to clean the artificial teeth 34 using a cleaning agent or a disinfectant harmful to a human body. Accordingly, a commercially available sterilization detergent is mainly used. However, the use of the commercially available sterilization detergent is not effective to remove the stains deposited on the artificial teeth 34.

Accordingly, as shown in FIG. 15, an artificial teeth cleaning device 35 is integrally formed with the apparatus 1 for producing photocatalytic reaction water and is immersed in water 31 stored in a water tank 33. By operating the apparatus 1 for producing photocatalytic reaction water, it is possible to clean the artificial teeth 34 efficiently. As shown in FIG. 15, for increasing the dissolved oxygen concentration in water, an oxygen generating agent 63 is immersed in water reservoir 33. The oxygen generating agent 63 generates bubbles upon being in contact with water, and oxygen contained in the bubbles are dissolved in water.

Accordingly, the water reservoir 33 having a predetermined volume is divided into two water reservoirs, wherein the apparatus 1 for producing photocatalytic reaction water according to the present invention is arranged in one divided water reservoir, and the artificial teeth 34 is immersed in the inside of another divided water reservoir 33 (cleaning reservoir). Due to such constitution, without adding other medicament or the like, this example can acquire the excellent cleaning effect, the excellent bacteria elimination effect, and the excellent bacteria sterilization effect. Convection of water can be generated by providing an underwater pump 61 between two water reservoirs thus realizing cleaning of the artificial teeth 34 in the inside of the cleaning reservoir with the photocatalytic reaction water.

Particularly, due to the contact of water containing active oxygen which contains abundant active oxygen species and hydrogen peroxide with the artificial teeth 34, dregs of the food and tar of tobacco deposited on the artificial teeth 34 are strongly oxidized and hence, stains can be easily removed from the artificial teeth 34.

Further, the photocatalytic reaction water possesses bacteria elimination/sterilization effect and hence, resident micro biota in the oral cavity adhering to the artificial teeth 34, and bacteria and Eumycetes which propagate in dregs of the food adhering to the artificial teeth 34 can be eliminated or sterilized thus keeping the artificial teeth 34 in a hygienic state.

Further, the water reservoir 33 is divided into two water reservoirs and hence, a low frequency ultrasonic vibrator 22 can be arranged in the inside of the cleaning reservoir without damaging the photocatalyst arranged in the photocatalytic reaction reservoir whereby stains can be separated by making use of a strong vibration force generated by the ultrasonic waves thus accelerating the oxidation decomposition reaction by the active oxygen species.

Further, active oxygen species and hydrogen peroxide included in the photocatalytic reaction water are subject to a reaction due to contact thereof with organic substances and hence, active oxygen species and hydrogen peroxide are readily converted into harmless substances such as water ($H_2O$), oxygen ($O_2$) and the like. Accordingly, it is possible to safely mount the artificial teeth 34 without adversely affecting a human body.

With the use of this artificial teeth cleaning system, it is also possible to clean medical equipment 62.

(iv) Example in which Apparatus for Producing Photocatalytic Reaction Water of the Present Invention is Used in Cleaning Tableware Next, there is described an example in which sterilizing and cleaning is performed by bringing photocatalytic reaction water into contact with tableware. For example, by arranging the apparatus 1 for producing photocatalytic reaction water according to the present invention in a water supply hose of a tableware washer, or by integrally forming the apparatus 1 for producing photocatalytic reaction water according to the present invention with the tableware washer for blowing photocatalytic reaction water produced by the apparatus 1 for producing photocatalytic reaction water to the tableware, it is possible to clean the tableware safe, effectively and hygienically without adding other medicament or the like.

That is, stains of food adheres to the tableware (a dish, chopsticks, a knife or a fork) used at table. Particularly, it is considered that stains of food is, in many cases, constituted of oil component originating from fish or meat or starch stains originating from cereals. These stains are liable to become a place where microorganisms propagate. Further, when the tableware with stains is used next time, these stains are brought into contact with food and hence, the tableware becomes unhygienic.

Accordingly, although the tableware used at table is cleaned by making use of detergents for the tableware together with tap water, cleaning of tableware is one of hard work out of housework.

Further, the tableware can be cleaned by making use of a tableware washer which cleans the tableware by blowing tap water to the tableware. The tableware washer can effectively remove oil stains with the use of detergents for the tableware, however, the tableware washer has difficulty in removing starch stains at present.

Here, by using photocatalytic reaction water produced by the apparatus 1 for producing photocatalytic reaction water according to the present invention as water blown from the tableware washer, not only oil stains, not to mention, but also starch stains or the like are oxidized by strong oxidizing ability which photocatalytic reaction water possesses and hence, it is possible to effectively remove oil stains, starch stains or the like. Further, by using photocatalytic reaction water as water blown from the tableware washer, the tableware is sterilized thus bringing the tableware into a hygienic state.

Further, even when the tableware is used for fermented food such as not to made with the use of sporaceous microorganisms at table, for example, as can be understood from a verification result of sterilization effect of the above-mentioned photocatalytic reaction water, it is possible to sufficiently eliminate the microorganisms.

Further, in this example, as a means for bringing photocatalytic reaction water into contact with tableware, there is described an example in which photocatalytic reaction water is blown to the tableware by the tableware washer. However, the means for bringing photocatalytic reaction water into contact with the tableware is not particularly limited to the above, and by storing photocatalytic reaction water in a container of a proper volume, the tableware may be immersed within the stored photocatalytic reaction water.

In this manner, by cleaning the tableware with photocatalytic reaction water, the tableware can be used in safe for a human body even when photocatalytic reaction water adheres to the tableware. Further, when the tableware is cleaned with photocatalytic reaction water, it is possible to bring the tableware into a sufficiently-hygienic state.

(v) Example in which Apparatus for Producing Photocatalytic Reaction Water of the Present Invention is Used in Cleaning Food Next, there is described an example in which sterilizing and cleaning is performed by bringing photocatalytic reaction water into contact with foods. For example, the apparatus 1 for producing photocatalytic reaction water according to the present invention is provided to a kitchen table for food processing so as to make use of photocatalytic reaction water for cleaning vegetables or fruits. With the provision of the apparatus 1 for producing photocatalytic reaction water, it is possible to acquire the safe and hygienic vegetables and fruits without adding other medicament or the like.

That is, vegetables and fruits are mainly cultivated outsides and are harvested and hence, there may be a case in which stains, microorganisms, insects or the like are adhered to the vegetables and the fruits. For example, vegetables of the leaf such as cabbages are cultivated at a relatively low position from the ground and hence, mud or the like is liable to be easily adhered to the vegetables. Further, vegetables of the leaf become a place where butterflies or moths lay eggs thereof, and larvae of the butterflies or moths propagate.

Accordingly, it is necessary to clean the vegetables or the fruits before the vegetables or the fruits are used for food. However, the mere washing of the vegetables or the fruits with water exhibits poor sterilization ability or cleaning ability and hence, such washing is hardly considered effective.

Although it is possible to clean the vegetables or the fruits using detergents for tableware, there exists a possibility that components of surfactant included in the detergents remains in the vegetables or the fruits after cleaning. Eating of food containing such components offends the feeling of consumer.

Here, the apparatus 1 for producing photocatalytic reaction water according to the present invention may be integrally formed with a kitchen table or the like. Due to such constitution, by making use of photocatalytic reaction water produced by the apparatus 1 for producing photocatalytic reaction water for cleaning the vegetables or the fruits, it is possible to effectively remove stains adhering to the vegetables or the fruits and, further, it is possible to sterilize insects, or microorganisms.

Further, agricultural chemical is sprayed to the vegetables or the fruits during cultivation in many cases. Accordingly, by cleaning the vegetables or the fruits using the photocatalytic reaction water, it is possible to decompose the agricultural chemical adhering to the vegetables or the fruits by active oxygen species or the like included in the photocatalytic reaction water thus reducing possibility of ill-affecting a human body.

Further, the photocatalytic reaction water includes a large quantity of so-called minus ion and hence, it is possible to clean the vegetable of the leaf while maintaining freshness in appearance without lilting the vegetable of the leaf.

As a means for bringing photocatalytic reaction water into contact with the vegetables or the fruits, by storing photocatalytic reaction water in a container of a proper volume, the vegetables or the fruits may be immersed within the stored photocatalytic reaction water. Further, the vegetables or the fruits may be sprayed with photocatalytic reaction water in mist or raindrop shape.

In this manner, by cleaning the vegetables or the fruits using photocatalytic reaction water, it is possible to sterilize or clean the vegetables or the fruits safely to a human body and hygienically without loosing freshness of the vegetables or the fruits.

(vi) Example in which Apparatus for Producing Photocatalytic Reaction Water of the Present Invention is Used for Cleaning Precision Instruments Next, a case in which the apparatus 1 for producing photocatalytic reaction water according to the present invention is used for cleaning the precision instrument is explained. For example, by arranging the apparatus 1 for producing photocatalytic reaction water according to the present invention between water supply hoses of a silicon wafer cleaner for manufacturing semiconductors or by integrally constituting the silicon wafer cleaner with the apparatus 1 for producing photocatalytic reaction water contacting the photocatalytic reaction water and bringing photocatalytic water produced by the apparatus 1 for producing photocatalytic reaction water into contact with a silicon wafer, it is possible to clean the silicon wafer safely and effectively without adding other medicament or the like.

That is, in a manufacturing step of semiconductors used in electronic equipment, along with the removal of unnecessary parts, there may be a case that fine dusts are generated on a silicon wafer. The dusts cause a defective product in the manufacture of semiconductors and hence, it is necessary to remove the dusts using the organic compound such as an organic solvent or a chelating agent. Here, the organic compound used for removing the dusts or the like is also adhered to the silicon wafer and hence, it is necessary to remove the organic compounds or the like.

Although hydrogen peroxide water is used for removing the organic compound or the like, handling of hydrogen peroxide water is dangerous and special treatment is necessary for discarding hydrogen peroxide water after use.

As an alternative of hydrogen peroxide water, with the use of photocatalytic reaction water produced by the apparatus for producing photocatalytic reaction water according to the present invention, the organic compound adhering to the silicon wafer can be removed.

Further, photocatalytic reaction water hardly affects a human body compared to hydrogen peroxide water even when photocatalytic reaction water is brought into contact with the human body thus exhibiting high safety whereby photocatalytic reaction water can be easily handled and, at the same time, the operability can be enhanced.

Further, although the oxidization ability of the active oxygen species included in photocatalytic reaction water is high, the active oxygen species are extremely unstable and hence, a reaction time of the active oxygen species is short whereby cleaning can be performed without obstructing a manufacturing process with respect to time even when semiconductors are continuously manufactured.

Here, in this example, the silicon wafer is named as the object to be cleaned. However, the object to be cleaned is not limited to the silicon wafer, and the present invention is applicable to cleaning of various precision instruments including a printed circuit board or electronic parts.

Figure 16:
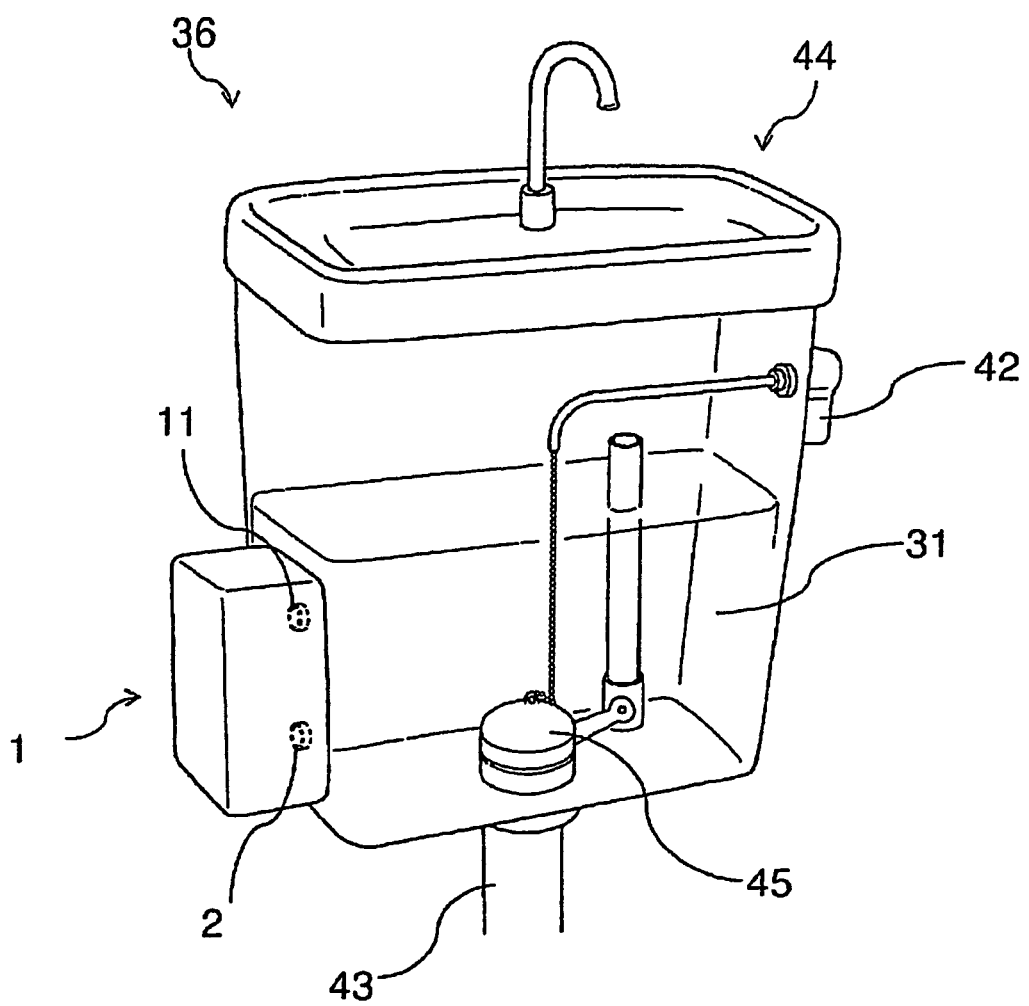
FIG. 16 is an explanatory view of the apparatus for producing photocatalytic reaction water according to the embodiment of the present invention.
Figure 17:
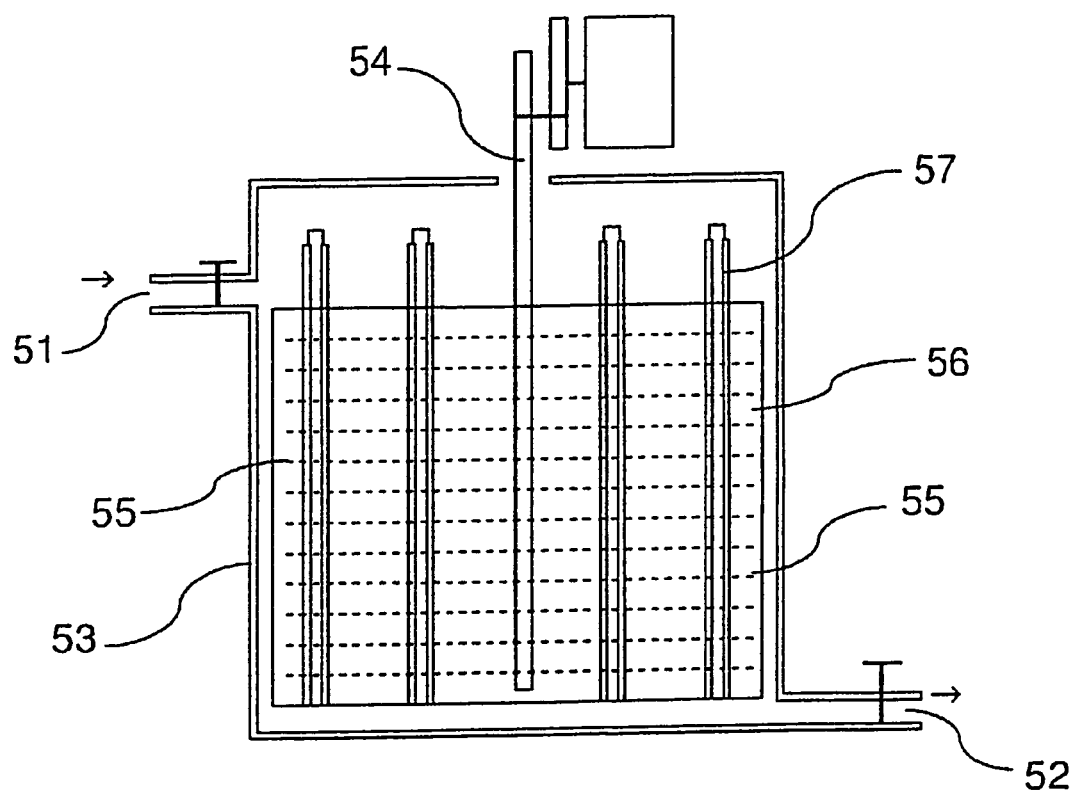
FIG. 17 is an explanatory view showing a prior art.
Figure 18:
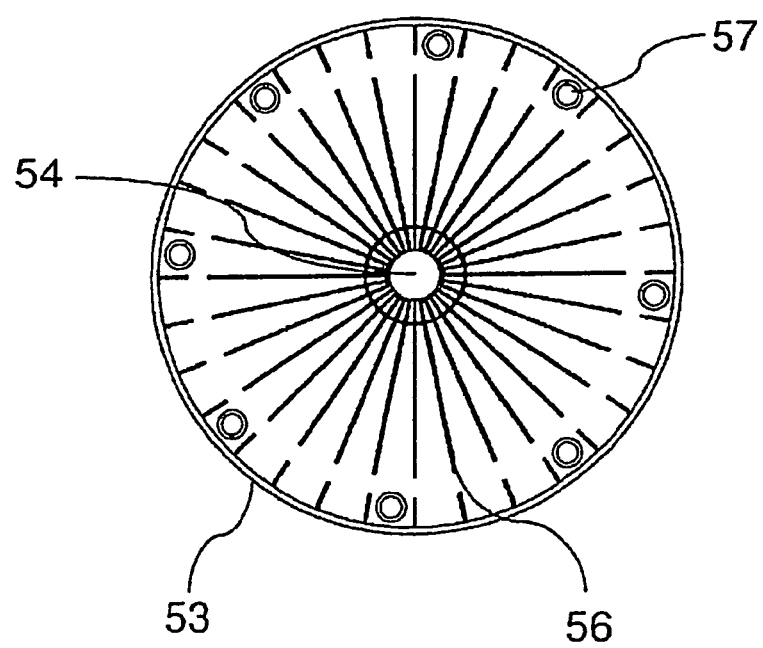
FIG. 18 is an explanatory view showing a prior art.

(vii) Example in which Apparatus for Producing Photocatalytic Reaction Water is Applied to Flushing Water Tank of Toilet Bowl Next, the explanation is made with respect to an example in which the apparatus 1 for producing photocatalytic reaction water according to the present invention is integrally arranged in a flushing water tank attached to a toilet system, and a toilet bowl is cleaned with photocatalytic reaction water in conjunction with FIG. 16. By cleaning the toilet bowl in such a manner, it is possible to keep the toilet system in a hygienic state without adding other medicament.

That is, the toilet bowl arranged in the toilet system is a portion where he/she relieves himself/herself and hence, the toilet bowl stains extremely easily. For example, once feces adheres to or is solidified on the toilet bowl or urine is petrified and deposited to the toilet bowl, it is hardly possible to remove feces or urine by rubbing with a blush.

Further, with respect to a type of toilet bowl which preliminarily stores water for flushing a waste material after relieving oneself to a sanitary pipe in a tank, the adhesion of stains is prevented by a method which mixes a commercially available cleaning agent such as a surfactant in stored water. However, no remarkable stains removing effect can be acquired with respect to already adhered stains.

Accordingly, the apparatus 1 for producing photocatalytic reaction water according to the present invention is formed of a toilet-bowl cleaning device 36 having the constitution as shown in FIG. 16, for example. Water 31 stored in a tank 44 is circulated in the apparatus 1 for producing photocatalytic reaction water, and photocatalytic reaction water is used as water stored in the tank 44 and hence, stains adhering to the toilet bowl is oxidized leading to the effective removal of the stains adhering to the toilet bowl. In FIG. 16, a blacklight 9 for radiating ultra violet rays to a photocatalytic body 20 stored in the apparatus 1 for producing photocatalytic reaction water, a water supply pump 32 for supplying water 31 in the tank 44 to the toilet bowl through a water supply port 2, and an the oxygen supply pipe 4 for mixing oxygen into water 31 is omitted.

Further, upon manipulation of a handle 42, faucet 45 is opened and hence, photocatalytic reaction water stored in the tank 44 is discharged into a toilet bowl not shown in the drawing through a communication pipe 43.

Further, the photocatalytic reaction water possesses the strong sterilization effect as described in the embodiment 3 and hence, contaminant bacteria adhering to the toilet bowl or a peripheral portion of the toilet bowl and bacteria in feces can be surely sterilized whereby it is possible to keep the toilet system in a clean state.

Further, by flushing waste material using the photocatalytic reaction water, the photocatalytic reaction water is brought into contact with the waste material even in a sanitary pipe through which the waste material discharged from the toilet bowl passes and hence, the stains on the sanitary pipe can be also removed whereby it is possible to prevent clogging of the sanitary pipe.

The photocatalytic reaction water also possesses an excellent deodorization effect and hence, it is possible to perform deodorization by decomposing odor after relieving oneself filled in the inside of the toilet system and odor which flows back from the sanitary pipe whereby this example provides a hygienic and comfortable environment in the inside of the toilet system.

Photocatalytic reaction water which is discharged from the toilet bowl together with the waste material is readily converted into water and oxygen after coming into contact with organic substances such as waste material or the stains and hence, there is no possibility that photocatalytic reaction water ill-affects the environment.

Theses advantageous effect can be acquired each time the waste material is discharged from the toilet bowl and hence, it is possible to always keep the toilet system in a hygienic state whereby efforts required for cleaning the toilet system can be remarkably reduced.

(viii) Example in which Apparatus for Producing Photocatalytic Reaction Water is Used for Washing Machine Next, there is described an example in which clothing or cloth is sterilized and cleaned by bringing photocatalytic reaction water into contact with the clothing or the cloth. For example, the apparatus 1 for producing photocatalytic reaction water according to the present invention is arranged in a washing machine or the like, wherein it is possible to bring the clothing or the cloth into an hygienic state by using photocatalytic reaction water for cleaning the clothing or the cloth.

For example, it is often the case that a person wears the clothing for long time and hence, sweats or oil components secreted from his/her body adheres to the clothing.

Accordingly, although it is necessary to wash the clothing after wearing, the mere washing of the clothing with water exhibits poor cleaning ability and hence, such washing is hardly considered effective.

Further, the clothing may be cleaned using a washing detergent or the like, components such as a surfactant included in a washing detergent may leave in the clothing thus becoming one of causes of allergy.

Accordingly, by using the photocatalytic reaction water produced by the apparatus 1 for producing photocatalytic reaction water according to the present invention as water to be supplied to a washing sink of a washing machine, stains adhering to the clothing can be effectively removed. Further, it is possible to eliminate the stains adhering to the clothing and, at the same time, bacteria in the clothing can be eliminated thus bringing the clothing in a hygienic state.

Further, a table cloth for wiping a surface of a table, a swabbing cloth for swabbing a floor or the like plays a role of wiping stains and hence, the stains are adhered to the cloth thus giving rise to a state in which microorganisms easily grow. By washing the cloth using the washing machine according to the present invention, it is possible to keep the cloth in a hygienic state and, at the same time, it is possible to prevent spreading of stains, microorganisms or the like by wiping.

Further, although an outer periphery of the washing sink is not usually observed from the outside, there is no contact between the outer periphery of the washing sink and materials to be washed thus providing a place where the stains adheres and the propagation of various bacteria progresses. By mounting the apparatus 1 for producing photocatalytic reaction water according to the present invention on the washing machine, these stains and the propagation of various bacteria on the outer periphery of the washing sink can be prevented.

(ix) Example in which Apparatus for Producing Photocatalytic Reaction Water is Used for Cleaning Rice Seeds Next, there is described an example in which rice seeds are sterilized and cleaned by bringing photocatalytic reaction water into contact with rice seeds. For example, by bringing the rice seeds into contact with photocatalytic reaction water produced by the apparatus 1 for producing photocatalytic reaction water according to the present invention before scattering on a seedling bed, it is possible to prevent the inhibition of growth of rice seeds due to bacteria, molds or the like.

That is, in growing rice, it is necessary to grow seedling for rice planting. However, it is necessary to make the rice seeds to bud out in a state in which water and air are present, there may be a case that microorganisms propagate and hence, and the propagated microorganisms impede the proper growth of the seedling or collapses the seedling.

Accordingly, it is necessary to sterilize the rice seeds spread on the seedling bed. However, there exists a possibility that after using a chemical agent for sterilization, the medicament flows out into a natural field thus ill-affecting the environment.

Further, it is considered that the medicament used in general which has the sterilizing ability considerably ill-affects the growth of the plants.

Accordingly, by bringing photocatalytic reaction water produced by the apparatus 1 for producing photocatalytic reaction water according to the present invention and the rice seeds into contact with each other thus sterilizing microorganisms or the like adhering to the rice seeds, it is possible to prevent the possibility that the efficacy of the medicament remains and ill-affects the growth of the plants and, at the same time, it is possible to prevent the medicament from ill-affecting the environment.

Further, it is unnecessary to acquire other medicament for sterilizing the rice seeds and hence, a cost necessary for rice growing can be lowered.

In this manner, by bringing the photocatalytic reaction water produced by the apparatus 1 for producing photocatalytic reaction water into contact with the object to be cleaned, it is possible to perform sterilization and cleaning while keeping the human body in a safe and hygienic state.

Industrial Applicability

In the apparatus for producing photocatalytic reaction water described in claim 1, light from the light source is radiated to the photocatalytic body to generate active oxygen species, and the active oxygen species are diffused in water thus imparting functions of the active oxygen species to water whereby an oxidation reaction which uses the water as a medium is utilized to perform at least one of the elimination of microorganisms, the elimination of parasites, and the elimination of protozoa.

To be more specific, by efficiently allowing the active oxygen species which having strong oxidizing ability which is generated only on a surface of the photocatalytic body to be separated from the photocatalytic body and to float in water, it is possible to effectively continuously generate the active oxygen species. Due to strong oxidation caused by the active oxygen species readily shifted into water, even when the apparatus for producing photocatalytic reaction water is miniaturized, it is possible to generate a large quantity of active oxygen species in water. Further, while assuring power saving and a compact size, the apparatus for producing photocatalytic reaction water can produce photocatalytic reaction water which possesses the excellent bacteria elimination effect, the excellent bacteria sterilization effect, the excellent cleaning effect, the excellent parasite elimination effect and the excellent bacteria sterilization effect.

In the apparatus for producing photocatalytic reaction water described in claim 2, the photocatalytic body is arranged around the light source for exciting the photocatalytic body. Accordingly, the light radiated from the light source can be effectively radiated to the photocatalytic body and hence, the apparatus can sufficiently generate active oxygen species in water.

In the apparatus for producing photocatalytic reaction water described in claim 3, the apparatus includes a photocatalytic reaction reservoir, the water supply pump which supplies water into the photocatalytic reaction reservoir, and the water discharge circuit which discharges photocatalytic reaction water from the photocatalytic reaction reservoir.

Here, the photocatalytic reaction reservoir arranges, in the inside of the water reservable sealed container, the photocatalytic body which generates active oxygen in water stored in the sealed container, the light source which radiates light for exciting the photocatalytic body, and the diffusion means which diffuses the active oxygen species generated on a surface of the photocatalytic body in water. The inner wall surface of the sealed container is formed of the mirror surface which reflects the light. Accordingly, the apparatus can continuously produce photocatalytic reaction water and, at the same time, light which reaches the wall of the sealed container without impinging on the photocatalytic body can be radiated to the photocatalytic body again by reflection and hence, it is possible to produce photocatalytic reaction water containing abundant active oxygen species.

Further, in the apparatus for producing photocatalytic reaction water described in claim 4, the light source for exciting the photocatalytic body utilizes sun light and/or artificial light. Accordingly, it is possible to selectively and effectively radiate sun light and artificial light to the photocatalytic body. When the sun light is selected, it is possible to radiate strong ultra violet rays to the photocatalytic body at a low cost, while when the artificial light is selected, it is possible to radiate ultra violet rays which have a predetermined wavelength to the photocatalytic body. Accordingly, the photocatalytic body can be efficiently excited and hence, it is possible to produce photocatalytic reaction water containing abundant active oxygen species.

Further, in the apparatus for producing photocatalytic reaction water described in claim 5, in using the sun light as the light source for exciting the photocatalytic body, a reflector such as the optical fibers or the prism is used for directly radiating light to the photocatalytic body in water. Accordingly, the sun light can be effectively radiated to the photocatalytic body and hence, it is possible to produce photocatalytic reaction water containing abundant active oxygen species.

Further, in the apparatus for producing photocatalytic reaction water described in claim 6, as the light source for exciting the photocatalytic body, an ultra violet ray radiation lamp which uses artificial light radiates ultra violet rays having a wavelength ranging from at least 350 to 370 nm. Accordingly, the photocatalytic body can be effectively excited and hence, it is possible to produce photocatalytic reaction water containing abundant active oxygen species.

Further, in the apparatus for producing photocatalytic reaction water according to claim 7, the photocatalytic body is an organic or inorganic filter body and a surface of the filter body is covered with a titania thin film. Accordingly, a surface area of the photocatalytic body can be increased and hence, it is possible to effectively produce photocatalytic reaction water containing abundant active oxygen species.

Further, in the apparatus for producing photocatalytic reaction water according to claim 8, the photocatalytic body is an aluminum-based metal filter body and a surface of the filter body is covered with a titania thin film. Accordingly, it is possible to impart flexibility to the photocatalytic body and, at the same time, it is possible to impart favorable workability to the photocatalytic body.

Further, in the apparatus for producing photocatalytic reaction water according to claim 9, the photocatalytic body is formed of a metal-made fiber body having a surface thereof preliminarily covered with an alumina film, and a surface of the photocatalytic body is covered with a titania thin film. Accordingly, the titania thin film is densely formed on the metal-made fiber body and hence, it is possible to effectively generate the active oxygen species and, at the same time, it is possible to enhance durability of the photocatalytic body.

Further, in the apparatus for producing photocatalytic reaction water according to claim 10, the alumina film of the metal-made fiber body is formed by heating the alumina film up to a temperature one half of a melting point of the aluminum-based metal which constitutes the metal fiber body at a rate of 5° C./min and, thereafter, by heating the metal-made fiber body up to a temperature immediately below the melting point of the aluminum-based metal. Accordingly, it is possible to densely form the alumina film on the metal-made fiber body thus increasing adhesiveness between the titania thin film and the metal-made fiber body. That is, it is possible to enhance durability of the photocatalytic body in water.

Further, in the apparatus for producing photocatalytic reaction water according to claim 11, the photocatalytic body is formed of a glass-made fiber body, a ceramics-made fiber body or a non-woven fabric having a surface thereof covered with a titania thin film. Accordingly, a surface area of the photocatalytic body can be increased and, at the same time, the photocatalytic body can be manufactured at a relatively low cost and hence, it is possible to manufacture the apparatus for producing photocatalytic reaction water at a low cost.

Further, in the apparatus for producing photocatalytic reaction water according to claim 12, titanium oxide which constitutes the titania thin film contains the anatase-type or rutile-type crystal structure. When the titanium oxide constitutes the anatase-type crystal structure, the photocatalytic body can be baked at a low temperature thus reducing energy necessary for baking the photocatalytic body and hence, it is possible to manufacture the apparatus for producing photocatalytic reaction water at a low cost. While when the titanium oxide constitutes the rutile-type crystal structure, the active oxygen species can be generated by radiating ultra violet rays contained in the sun light and, at the same time, the active oxygen species can be also generated by radiating light having wavelengths within a wavelength range of visible light.

Further, in the apparatus for producing photocatalytic reaction water according to claim 13, a diffusion means which diffuses the active oxygen species in water is ultrasonic waves of 100 kHz or more generated by an ultrasonic wave oscillator and/or water flow generated by a water pump for moving the photocatalytic body and/or water. Accordingly, it is possible to readily separate the active oxygen species generated on the surface of the photocatalytic body from the photocatalytic body in water.

Further, in the apparatus for producing photocatalytic reaction water according to claim 14, water which is brought into contact with the photocatalytic body is water containing oxygen at high concentration. Accordingly, the more active oxygen species can be generated by the photocatalytic body and hence, it is possible to produce photocatalytic reaction water containing abundant active oxygen species.

Further, in the apparatus for producing photocatalytic reaction water according to claim 15, water containing oxygen at high concentration is produced by bringing water into contact with at least one of oxygen, air and ozone. Accordingly, it is possible to efficiently dissolve oxygen in water and, further, it is possible to effectively generate more active oxygen species.

Further, in the apparatus for producing photocatalytic reaction water according to claim 16, a sterilizing action is generated by a sterilizing lamp which radiates ultra violet rays having a wavelength ranging from 254 to 265 nm upstream of a position where a sterilizing action by the photocatalyst is generated, downstream of the position or at the position. Accordingly, microorganisms included in water which is brought into contact with the photocatalytic body or photocatalytic reaction water produced by the apparatus for producing photocatalytic reaction water can be further effectively eliminated and sterilized.

The invention claimed is:

1. An apparatus for producing photocatalytic reaction water, comprising:
   a photocatalytic reaction reservoir comprising:
      a photocatalytic body comprising fibers having free distal end portions that are configured to oscillate when subjected to ultrasonic wave vibrations;
      a light source configured to radiate light that excites the photocatalytic body;
      an ultrasonic wave oscillator configured to impart ultrasonic wave oscillations of 100 kHz to 500 kHz to the photocatalytic body; and
      an oxygen supply pipe configured to increase a concentration of oxygen in water before the water is brought into contact with the photocatalytic body, wherein the photocatalytic body is formed of a wooly aggregate wherein a photocatalyst is applied to a surface of the fibers by coating,
   a water conduit supply pump configured to supply water into the photocatalytic reaction reservoir; and
   a water conduit configured to discharge the photocatalytic reaction water from the photocatalytic reaction reservoir, wherein the apparatus is configured to:
      generate active oxygen species on a surface of the photocatalytic body in contact with water by radiating light from the light source to the photocatalytic body; and
      allow the free distal end portions of the fibers that are present in the photocatalytic body to act as free ends under the ultrasonic wave vibrations so that water flows on a surface of the fibers at a high flow rate due to the ultrasonic wave vibrations of the fibers, whereby the active oxygen species are efficiently separated from the photocatalytic body, and a large quantity of the active oxygen species floats in water; and
      produce the photocatalytic reaction water that eliminates at least one of a microorganism, a parasite, and a protozoon by an oxidation reaction, wherein:
         the photocatalytic reaction reservoir comprises a water reservable sealed container,
         the photocatalytic body, the light source, and the ultrasonic wave oscillator are located within the sealed container and the photocatalytic is body is arranged around the light source,
         an inner wall surface of the sealed container is formed of a mirror surface that reflects light, and
         the fibers are formed of a metal-made fiber body having a surface thereof preliminarily covered with an alumina film, and a surface of the photocatalytic body is covered with a titania thin film.

2. The apparatus for producing photocatalytic reaction water of claim 1, wherein the alumina film of the fibers are formed by heating the alumina film up to a temperature one half of a melting point of the aluminum-based metal which constitutes the metal fiber body at a rate of 5° C./min and, thereafter, by heating the metal-made fiber body up to a temperature immediately below the melting point of the aluminum-based metal.

3. The apparatus for producing photocatalytic reaction water of claim 2, wherein the light source for exciting the photocatalytic body is configured to radiate sun light and/or artificial light.

4. The apparatus for producing photocatalytic reaction water of claim 3, wherein the light source comprises an ultraviolet ray lamp configured to radiate ultraviolet rays having a wavelength ranging from 350 to 370 nm.

5. The apparatus for producing photocatalytic reaction water of claim 4, wherein the titania thin film comprises titanium oxide having an anatase or rutile crystal structure.

6. The apparatus for producing photocatalytic reaction water of claim 5, wherein the oxygen supply pipe is configured to supply at least one of oxygen, air, and ozone to the water.

7. The apparatus for producing photocatalytic reaction water of claim 6, wherein the light source comprises optical fibers or a prism configured for directly radiating light to the photocatalytic body.

* * * * *